United States Patent [19]

Fischer

[11] 4,304,238

[45] Dec. 8, 1981

[54] PROGRAMMABLE DEMAND PACER

[75] Inventor: David J. Fischer, Arden Hills, Minn.

[73] Assignee: Cardiac Pacemakers, Inc., St. Paul, Minn.

[21] Appl. No.: 62,924

[22] Filed: Aug. 2, 1979

Related U.S. Application Data

[63] Continuation of Ser. No. 880,895, Feb. 24, 1978, which is a continuation of Ser. No. 724,019, Sep. 16, 1976, abandoned.

[51] Int. Cl.³ ............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,557,796 | 1/1971 | Keller, Jr. et al. | 128/419 PG |
| 4,049,004 | 9/1977 | Walters | 128/419 PG |
| 4,095,603 | 6/1978 | Davies | 128/419 PG |
| 4,132,233 | 1/1979 | Hartlaub | 128/419 PG |

Primary Examiner—William E. Kamm
Attorney, Agent, or Firm—Orrin M. Haugen; Thomas J. Nikolai

[57] ABSTRACT

An implantable demand-inhibit type cardiac pacer for producing artificial stimulating pulses of a desired repetition rate and of a desired pulse width in the absence of normal R-wave activity in the patient's heart. The pacer is implemented principally from integrated circuit digital logic components and includes programmable registers, which when addressed by an externally applied code word of a predetermined format, allows the pulse width as well as the pulse rate of the pacer pulses to be changed to different desired values. Also incorporated in the pacer of this invention is circuitry which allows testing of the implanted energy source so that a physician can readily determine whether the energy source has discharged to a point where replacement is indicated.

A dual refractory period for paced beats and normal beats is provided along with digital circuits for insuring proper operation even in the presence of extraneous noise signals. Furthermore, fail-safe circuitry is provided to insure that the patient's heart will be properly stimulated even where, through a programming error, an unacceptable pacer pulse width or rate is entered into the programmable registers.

10 Claims, 11 Drawing Figures

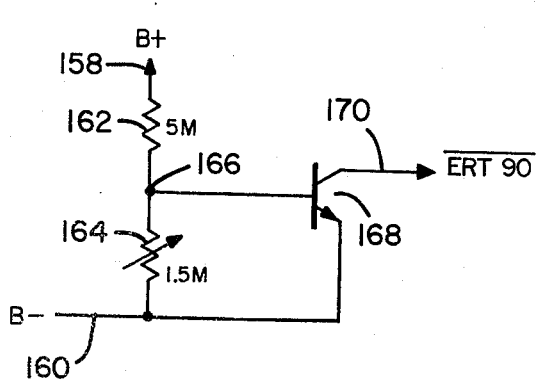
_Fig. 3a_
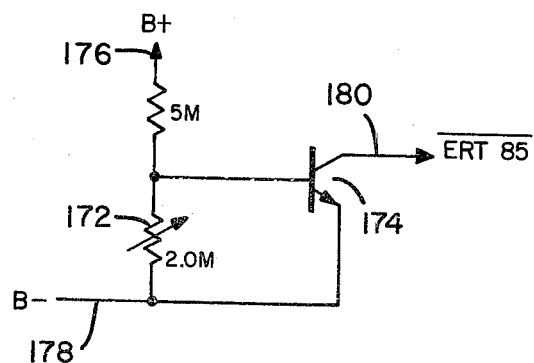
_Fig. 3b_
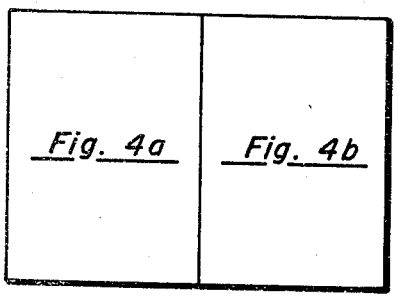
_Fig. 4_
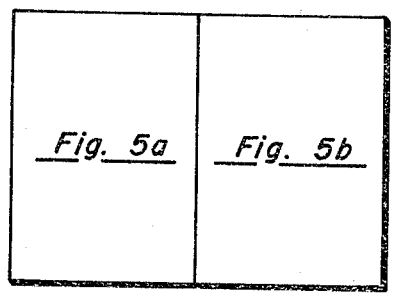
_Fig. 5_

PROGRAMMABLE DEMAND PACER

CROSS-REFERENCE TO RELATED APPLICATIONS

This is a Continuation of application Ser. No. 880,895, filed Feb. 24, 1978, which application Ser. No. 880,895 was a Continuation of application Ser. No. 724,019, filed Sept. 16, 1976, now abandoned.

BACKGROUND OF THE INVENTION

This invention relates generally to electronic pacer devices for providing artificial electrical stimulation to the heart of a patient and more specifically to an improved pacer of the demand-inhibit type which incorporates digital logic circuitry in the pulse generator for providing several unique features not presently found in commercially available pacers.

In the normal heart, electrical signals are generated and appear in the atrium at a rate of approximately 60 to 120 times per minute, depending upon the physical activity of the individual. About 0.1 seconds following the generation of each atrial signal, a signal is transmitted to the ventricle, causing it to contract and force blood from the ventricle through the body. Following the ventricular contraction, the heart experiences a refractory delay period which persists approximately 0.4 seconds and during which the heart is unresponsive to electrical stimulation.

An often observed abnormality of the heart is its failure to regularly or periodically generate atrial signals. Atrial signals may be generated with perfect regularity but then, suddenly, cease altogether or occur at an abnormally low rate. To compensate for such a defect the so-called "demand-inhibit" pacer is a practical solution. Such a device applies stimulating pulses to the ventricle by means of surgically implanted electrodes only when natural pulses do not occur spontaneously. As long as natural pulses occur at a desired rate, the implanted pacer provides no stimulation. However, when the natural or spontaneous ventrical pulses fail to occur or occur at irregular intervals the pacer comes into play to provide artificial stimulation at a desired rate.

Prior art heart pacers as well as the pacer of the present invention include a simulated refractory delay period. The reason for including a simulated refractory delay in the pacer circuitry is to ignore spontaneous signals developed by the heart which occur within a prescribed time period following application of an artificial stimulating pulse.

The pacer of the present invention operates asynchronously at a predetermined frequency (e.g., 100 beats per minute) when a permanent magnet is applied over the implanted pacer. This is the so-called "magnetic rate". The unit will remain in the magnetic rate mode as long as the permanent magnet is in proximity to the implanted pacer device and for a maximum of 2,256 milliseconds after removal of the magnet. Immediately after the magnetic rate interval, the pacer will operate asynchronously at the programmed nominal rate for six pacer pulses. This allows the pulse generator to be checked for both magnetic ate and nominal rate with the use of an externally applied magnetic field.

Another aspect of the present invention is the incorporation of an Elective Replacement Time indicator feature. The ERT indicator is tied in with the magnet rate of 100 beats per minute, therefore, a magnet is also used to check the ERT. When the output of the implanted energy source (battery) has decreased ½ of the way to ERT, the magnetic rate will drop to 90 beats per minute. When the ERT is reached, the magnetic rate will drop to 85 beats per minute. Therefore, a technician can readily determine by sensing the frequency or rate of pacer pulses when in the magnetic rate mode just when further surgery may be required to replace the energy source.

The pacer circuit of the present invention also includes noise protecting circuitry. Specifically, a bandpass amplifier is used as a signal discriminator which attenuated unwanted signals, i.e., EMI, T-waves, 60 cycle pickup, etc., but passes signals containing the fundamental frequency component of R-waves. Thus, all unwanted signals are filtered and only desirable signals are passed. Noise protection is afforded by the fact that the pacer of the present invention includes apparatus for monitoring the pacer inputs during refractory intervals. If for any reason, electrical noise should pass through the bandpass amplifier, a noise detection circuit, including a chain of bistable flip-flops, takes over and switches the pulse generator into its asynchronous mode in which state it remains until the noise source is no longer present.

Another feature of the pacer of the present invention is the incorporation of a dual refractory system. More specifically, the circuitry incorporated in the pacer provides a 256 millisecond refractory period following the occurrence of a natural heartbeat and a 320 millisecond refractory period following a heartbeat that is a result of an artificial stimulating pacer pulse. During the final 64 milliseconds of the refractory periods, the pulse generator will be monitoring the heart electrodes for electrical signal activity, but will not allow the resetting of the pulse generator timing. This too is important in rendering the device immune from external noise.

The pacer system of the present invention also permits reprogramming of the rate of generation of pacer pulses as well as the width of such pulses. Programming is accomplished by means of an external console into which an operator may enter a code combination which functions to unlock circuitry in the implanted unit to allow new pulse rate and pulse width information to be entered. This is accomplished by means of an electromagnet which is positioned outside of the body but in proximity to the implanted pacer unit. The electromagnet is pulsed by the control circuits in the console and operates a magnetic reed switch which is found in the implanted circuitry. A three digit pulse train is employed to allow programming of the pulse generator. Before a new pulse rate may be entered, the external programming unit must first present a certain preselected code, such as a 5-3-4 code to the reed switch. Similarly, before the width of the pacer pulse may be changed, a second preselected code, such as a 5-3-2 code must be entered.

Upon application of the first pulse of the initial digit (5) the circuitry will revert to its magnetic rate mode (100 BPM) and will remain there until the programming operation has been completed. When programming in a new pulse rate, the operator initially presents a 5-3-4 address code to the pulse generator. Once the pulse rate generator is addressed, a single pulse from the programmer initiates the pulse period. A second pulse from the programmer terminates the pulse period at the desired pulse interval. This interval, in conjunction with the pulse generator internal clock, allows the programming of any rate between 30 and 120 BPM. The programming time for any rate between 30 and 120 BPM is 2,256 milliseconds. Regardless of the rate programmed, i.e. between 30 and 120 BPM, the pulse generator will remain in the magnetic rate for the full 2,256 milliseconds.

Should an abnormally long or short pulse rate be supplied to the pulse generator, the following will occur. In the case of an excessively long rate, e.g., greater than 2,048 milliseconds, the pulse generator will remain in the paced magnetic rate mode (100 BPM) until an acceptable rate is inserted. If the rate is less than 496 milliseconds, the pulse generator will remain in the paced magnetic rate mode until an acceptable rate is programmed.

An alternate width for the pacer pulse is programmed in a somewhat different manner. Once the pulse generator is addressed, a pulse train corresponding to a particular pulse width is presented to the pulse generator. The minimum width is assured by a hard wired connection within the pacer unit and is 0.05 milliseconds. This is incorporated to guard against failure to enter any width count after successfully addressing the pulse generator by the 5-3-2 code. In the event that an excessive number of pulses are included in the pulse train, the pulse generator will reach its maximum width of 3.2 milliseconds and recycle back to 0.10 milliseconds. It will continue to cycle until no more pulses are received. Following the reprogramming operation, the pulse generator switches to its asynchronous mode for six pacer pulses and then to the demand mode.

The three digits of the unlocking codes are transmitted in three consecutive 68 milliseconds time frames. The first digit time frame overlaps the pulse generator's first digit time frame by 4 milliseconds to ensure entry of the digit. The second digit time frame overlaps the pulse generator's second digit time frame by 8 milliseconds and the third digit overlaps by 12 milliseconds. This overlap will ensure that the unlocking code is entered even if the clock frequency in the implanted unit has drifted somewhat from its design value.

SUMMARY OF THE INVENTION

It is, accordingly, the principal object of this invention to provide a new and improved pulse generator for an artificial cardiac pacer of the demand, R-wave inhibit type.

It is a further object of this invention to provide an artificial pacer wherein digital rather than analog circuitry is utilized to thereby allow microminiaturization to a degree heretofore not possible.

Still another object of the invention is to provide a pacer circuit in which the rate of production of pacer pulses and the width of the pacer pulses may be selectively changed without the need for further surgery.

A still further object of the invention is to provide a pacer which is highly insensitive to external noise.

Yet still another object of the invention is to provide a new and improved heart pacer network which allows simplified testing of the condition of the energy source used therein without the need for surgically removing same for inspection.

A yet still further object of the invention is to provide in a pacer of the type described, a combination lock circuit which allows reprogramming of the pacer rate and/or pacer pulse width only when a proper unlocking code has been applied to the unit by means of an external program.

The foregoing and additional advantages and characterizing features of the present invention will become clearly apparent from a reading of the ensuing detailed description thereof together with the included drawings wherein:

BRIEF DESCRIPTION OF THE DRAWINGS

FIGS. 3a and 3b are schematic electrical diagrams of a portion of the circuitry used to implement the ERT check feature;

FIG. 4 shows the way that FIGS. 4a and 4b should be positioned to yield a composite schematic diagram.

FIG. 5 shows the way that FIGS. 5a and 5b should be positioned to yield a composite schematic diagram.

DESCRIPTION OF THE PREFERRED EMBODIMENT

Figure 1:
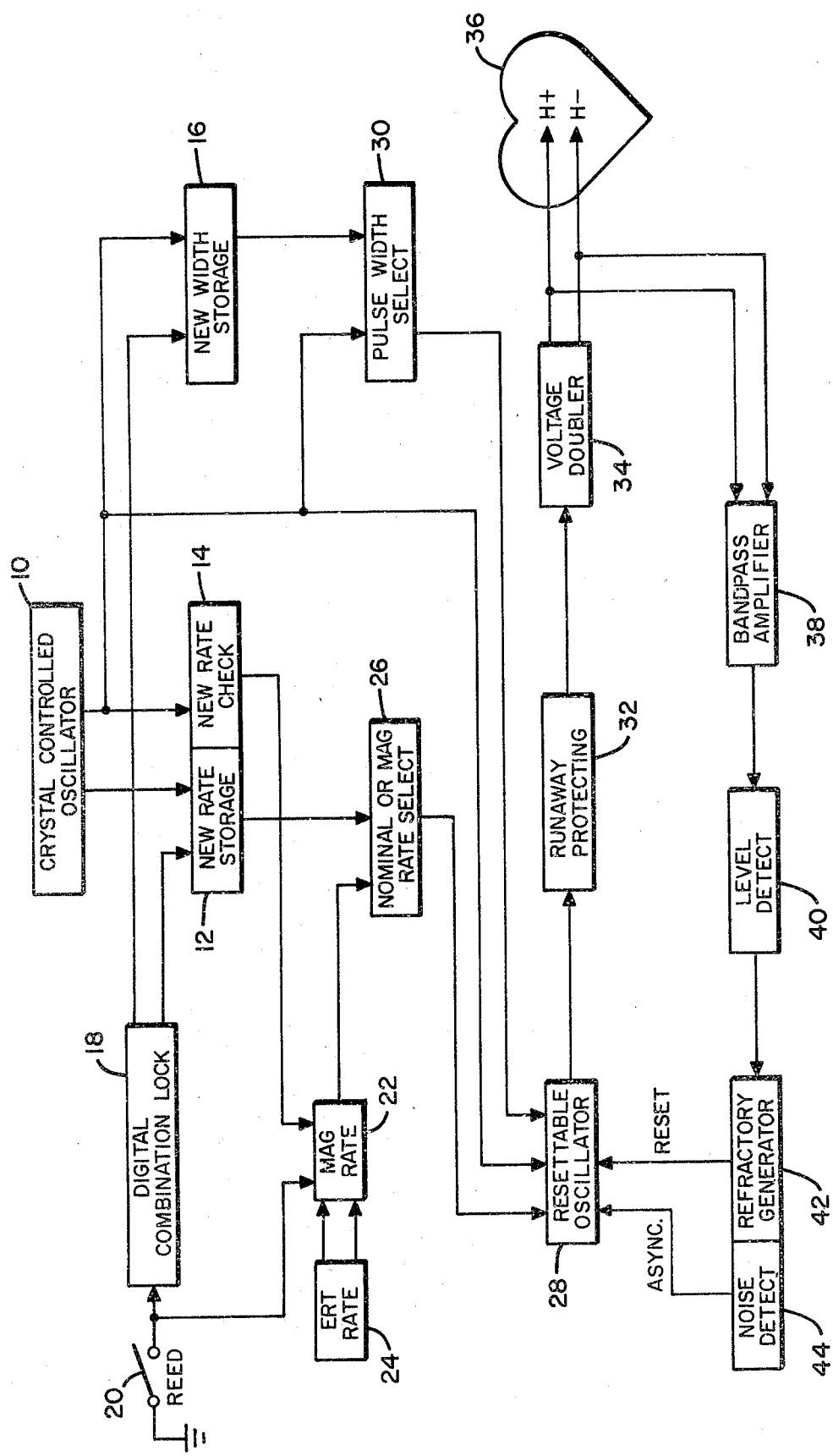
FIG. 1 is a functional block diagram of the cardiac pacer according to the present invention.

Referring first to FIG. 1 there is shown a functional block diagram of the preferred embodiment of the present invention. Identified by numeral 10 is a crystal controlled oscillator which serve as the main timing element. The crystal controlled oscillator may be designed to produce regularly occurring square wave pulses at a rate of 10 KHz, for example. Where pulses of a lower frequency are required, a conventional frequency dividing network may be employed. The output from the oscillator is connected to a block 12 labeled "New Rate Storage" as well as to a block 14 labeled "New Rate Check". The main timing oscillator 10 also provides clock pulses to the block 16 labeled "New Width Storage". Both the New Rate Storage element 12 and the New Width Storage element 16 are under the control of a digital combination lock element 18. Thus, as will be fully explained hereinbelow, before a new pulse rate value or a new pulse width value can be programmed into the apparatus, the digital combination lock 18 must have a predetermined code applied thereto to enable the new entries to be made. The digital combination code can only be applied to the element 18 when a magnetically operable reed switch is actuated. This reed switch 20 also controls the element 22 labeled "Mag Rate", the purpose of which will become more apparent from discussions which follow. The functional block labeled 24 symbolically represents the circuitry whereby a physician may determine the voltage of the implanted energy source for the purpose of determining whether a surgical replacement of the energy source should be made. The manner in which this is accomplished will also be described when the detailed circuitry forming the preferred embodiment is discussed. For now, however, it is sufficient to say that the Elective Replacement Time (ERT) is determined when the pacer is operating in its so-called "magnetic rate mode" and this is the reason that the functional block 24 is shown as being coupled to the Magnetic Rate block 22.

In a similar fashion, once a new pulse repetition has been entered into the device, it is desirable to check this new rate to see that it is properly entered. This is also accomplished when the apparatus is in its mag rate mode and hence, the functional block 14 is also shown as being coupled to the Mag Rate block 22.

The block 26 entitled "Nominal or Mag Rate Select" receives as an input the output from the New Rate Storage block 12 and the Mag Rate block 22 and functions to select one or the other for applying or steering the output therefrom to the Resettable Oscillator 28 which is the device which produces the pacer pulses upon demand for application to the heart of the patient. The Resettable Oscillator 28 is also controlled by the Crystal Controlled Oscillator 10 and by a block labeled "Pulse Width Select" 30. This latter device functions to apply signals either from the Crystal Controlled Oscillator 10 or from the New Width Storage element 16 to the Resettable Oscillator 28.

The block labeled "Runaway Protecting" 32 is shown as being connected to the output of the Resettable Oscillator 28. As will be fully explained, the Runaway Protecting network 32 serves to insure that the pulse rate will never exceed 130 beats per minute (BPM) irrespective of the outut from the Resettable Oscillator 28. In a reprogrammable rate type demand pacer of the type described herein, such as protecting network is deemed necessary to protect the patient in the event that a malfunction of the main timing circuit causes the Resettable Oscillator to run at too high a pulse rate.

As shown in FIG. 1, the output of the Runaway Protecting block 32 is coupled to a Voltage Doubler network 34. This circuit operates in a conventional fashion to approximately double the amplitude of the pulses applied to its input and insures that for a desired battery potential, the stimulating signals applied to the heart load 36 by way of the surgically implanted electrodes labeled H+ and H− will be sufficient to provide the degree of stimulation required.

As in all demand type pacers, means are provided for sensing normal heart activity. As is shown in the functional block diagram of FIG. 1, the same electrodes H+ and H− that couple the heart stimulating pulses from the output of Voltage Doubler 34 are used to pick-up or sense the electrical output from the heart occurring during normal activity. These signals are fed through a Bandpass Amplifier 38, and a Level Detect network 40 to a so-called "Refractory Generator" 42. In the pacer of the present invention, a dual refractory arrangement is provided. More specifically, a refractory period of 256 milliseconds is provided for a sensed heart signal and a 320 millisecond refractory period is provided for an artifically stimulated beat. During the last 64 milliseconds of these refractory periods, the Amplifier 38 will be monitoring the heart electrodes for electrical activity, but will not allow resetting of the Resettable Oscillator 28.

A functional block 44 labeled "Noise Detect" is shown as being associated with the refractory generator 42. During the last 64 milliseconds of the two refractory intervals mentioned above, the electrical activity of the pacer inputs is being monitored. If for any reason, electrical noise signals should pass through the bandpass amplifier 38, the noise detection circuit 44 takes over and switches the Resettable Oscillator 28 into its "asynchronous mode". The pulse generator 28 will then be operating asynchronously at its nominal rate until the noise signals disappear.

Now that the overall organization of the implantable demand type pacer of the present invention has been described with the aid of the functional block diagram of FIG. 1, the details of the various electronic circuits used to implement the system will be described. Following that, a description will be given of the mode of operation.

Figure 2:
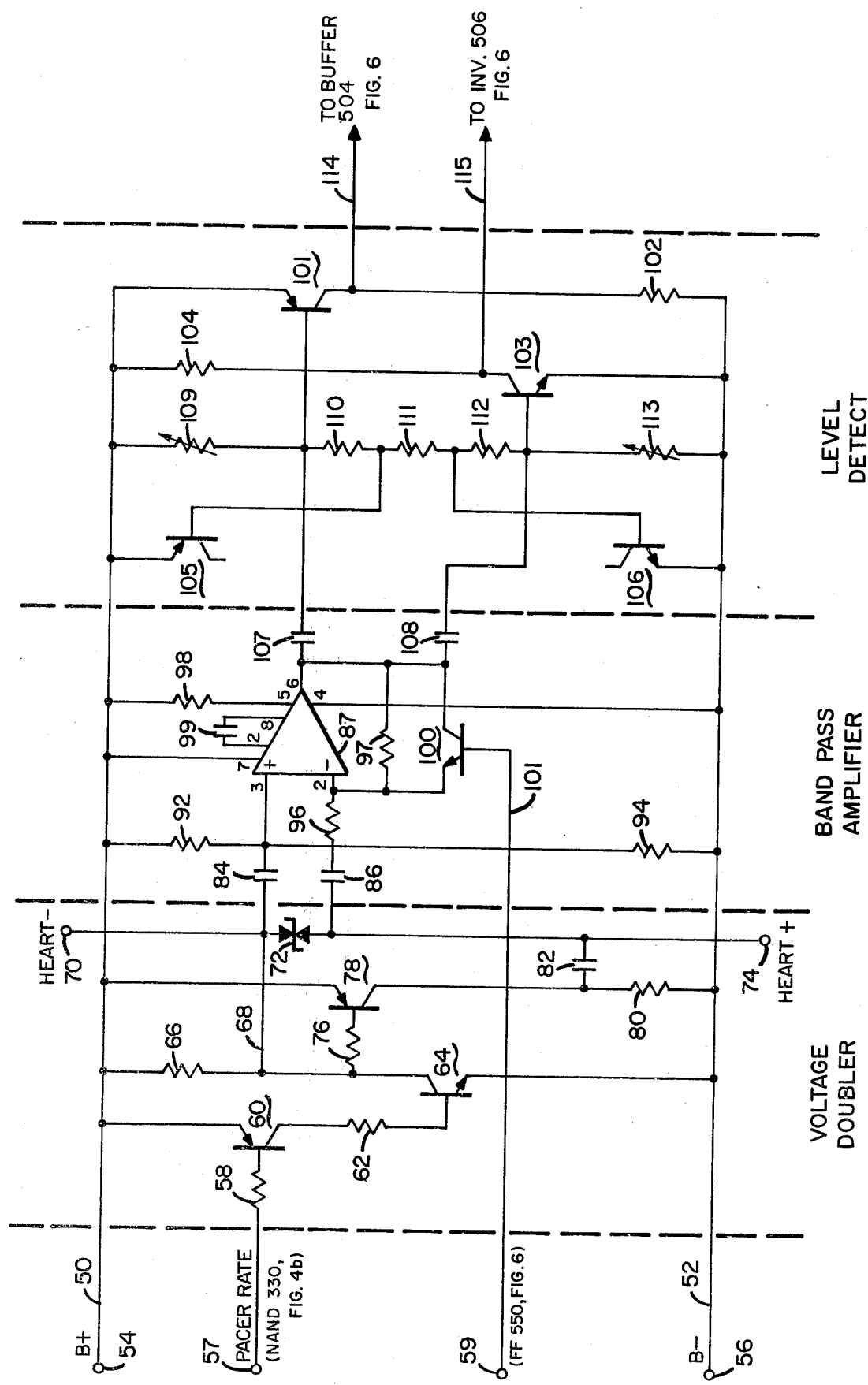
FIG. 2 is a schematic electrical diagram of the voltage doubler, bandpass amplifier, and level detector circuitry incorporated in the pacer of the present invention.

Referring to FIG. 2, there is shown by means of a schematic electrical diagram the circuitry used to implement the Voltage Doubler network 34, the Bandpass Amplifier 38, the Level Detect 40 and a portion of the Refractory Generator 42 shown in the block diagram of FIG. 1. In this figure there is shown a positive bus 50 and a negative bus 52 which are adapted to be connected at the B+ and B− terminals 54 and 56 to a source of direct current which, in the preferred embodiment, may be Lithium Iodide cell. As is well known in the art, Lithium Iodide batteries are especially well suited for use in implanted pacemakers because of their relatively long life and the absence of gas generation during discharge thereof.

A resistor 58 couples the output from the pacer rate gate 330 connected to terminal 57 (FIG. 4b) to the base electrode of a PNP transistor 60. The emitter electrode of transistor 60 is connected to the positive bus while the collector electrode thereof is coupled by a resistor 62 to the base electrode of an NPN transistor 64. The emitter electrode of transistor 64 is connected to the B− bus 52. The collector electrode of transistor 64 is coupled to the positive bus by means of a resistor 66 and to the negative heart terminal 70 by a conductor 68. A bidirectional diode 72, connects the collector electrode of the transistor 64 (via conductor 68) to the positive heart electrode terminal 74. Electrode terminals 70 and 74 are adapted to be connected to surgically implanted electrodes affixed to the heart of the patient. They serve to apply artificial stimulating pulses to the heart and also act as the pickup means for sensing electrical output from the heart occurring during normal contractions thereof.

A resistor 76 couples the collector electrode of tranistor 64 to the base or control electrode of a PNP transistor 78. The emitter electrode of transistor 78 is connected directly to the positive bus 50. Its collector electrode is coupled through a resistor 80 to the negative bus 52. A voltage doubling capacitor 82 is connected between the collector electrode of the PNP transistor 78 and the positive heart terminal 74.

Coupling capacitors 84 and 86 couple the bipolar signals developed during normal heart contractions to the input terminals of a differential bandpass amplifier 87. A voltage divider including the series connected resistors 92 and 94 is connected directly between the positive bus 50 and the negative bus 52 and the junction between these two resistors is connected to the positive input terminal of the differential bandpass amplifier 87. This arrangement determines the operating point for the differential amplifier. A resistor 96 in series with the coupling capacitor 86 is connected to the minus terminal of differential amplifier 87. Further, a feedback resistor 97 is connected between the outut terminal of the differential amplifier 87 and the minus input terminal thereof. The combination of resistors 96 and 97 establish the voltage gain of the amplifier 87. The resistor 98 coupled between the positive bus 50 and an auxiliary terminal of the amplifier 87 establishes the bias current for the amplifier. Thus, there will be developed at the output of the differential amplifier 87 an amplified signal which is proportional to the differential signal developed across the implanted heart electrode terminals 70 and 74.

Figure 6:
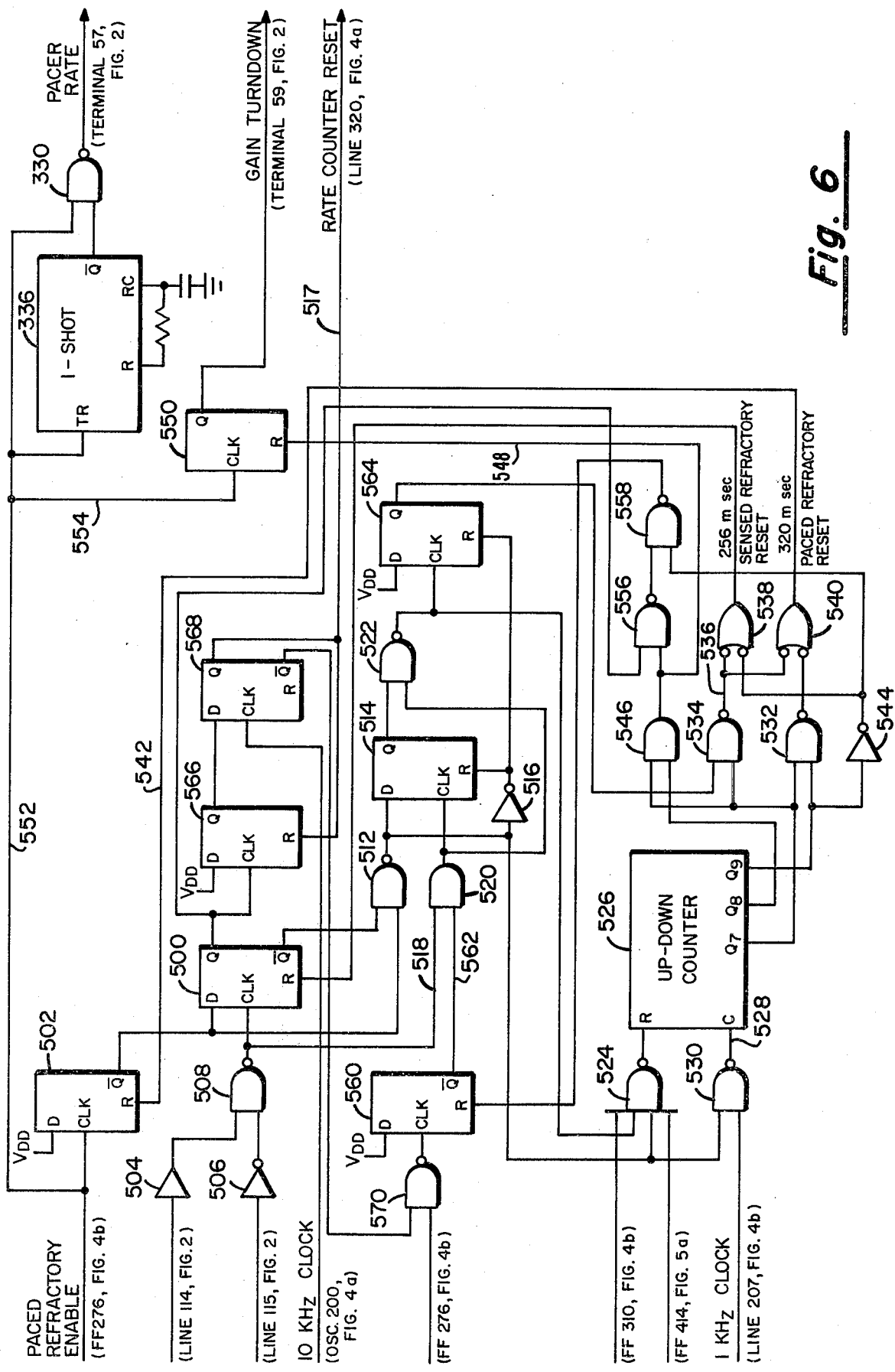
FIG. 6 illustrates by means of a digital logic diagram the circuitry utilized to establish the dual refractory periods and to provide noise detection control.

An NPN transistor 100 has its emitter-collector path connected directly in parallel with the feedback resistor 97. The base electrode thereof is coupled by way of a conductor 101 to the output of flip-flop 550 (FIG. 6). As will be explained more fully when the details of FIG. 6 are set forth herein, the flip-flop 550 provides a signal to the transistor 100 for a predetermined time interval during which the gain of amplifier 87 is turned down to zero. Thus, the amplitude of the output signal from the differential amplifier 87 is decreased during the time that the flip-flop 550 is set.

The resistors 92, 94, 96 and 97 along with the coupling capacitors 84 and 86 form a low pass filter network. The feedback capacitor 99 associated with the amplifier 87 creates a high pass filter network. Thus, the combination of these components with the differential amplifier 87 can be considered as creating a bandpass amplifier. The component values comprising this bandpass amplifier are chosen to give a center frequency of approximately 31 Hz with a lower 3 db point of 12 Hz and an upper 3 db point of 62 Hz. As such, this bandpass amplifier arrangement acts as a discriminator, attenuating unwanted signals which may be generated by extraneous sources outside of the body of the patient. However, it passes signals containing the fundamental frequency components of R-wave signals produced by the heart muscle. The output from the bandpass amplifier stage is applied via a coupling capacitor 107 to the base electrode of a PNP transistor 101 whose emitter electrode is tied to the positive bus 50 and whose collector electrode is coupled through a bias resistor 102 to the negative bus 52. The output from the bandpass amplifier is also applied through a coupling capacitor 108 to the base of an NPN transistor 103 having its collector electrode coupled through a bias resistor 104 to the positive bus 50 and its emitter electrode connected directly to the negative bus 52. ap The switching threshold for the PNP transistor 101 is established by a voltage divider including the series connected resistors 109,110,111,112 and 113 which are connected between the positive bus 50 and the negative bus 52. A transistor 105 having its collector open has its emitter tied directly to the positive bus 50 and its base electrode tied to the junction point formed between series connected resistors 110 and 111. Similarly, a transistor 106 of opposite conductivity type has its collector electrode open and its emitter electrode tied to the negative bus 52 and its base electrode connected to the junction point formed between the series connected resistors 111 and 112. Thus, the transistors 105 and 106 function as semiconductor diodes. As was inferred above, the resistors 109, 110, 111, 112, and 113 along with the diode connected transistors 105 and 106 establish the switching point for the level detect transistors 101 and 103. The resistors 109 and 113 can be considered as trimming devices which are used to precisely set the exact switching point for the level detecting network.

It is sufficient at this point merely to mention that the level detector network senses the output from the bandpass amplifier 10 and produces a pulse on the output lines 114 or 115 associated respectively with the level detect transistor 101 and 103, whenever the output from the bandpass amplifier exceeds a predetermined threshold in either a positive or a negative sense. The output signals which appear on lines 114 or 115 are fed directly into the buffer amplifier 504 and inverter 506 in FIG. 6.

Resistor 109 is trimmed so that for the desired negative excursion of the amplifier 87 output, transistor 101 will turn on, causing line 114 to go positive. This signal propagates through buffer 504 causing the output of gate 508 to go positive. In a like manner, resistor 113 is trimmed such that for the desired positive excursion, transistor 103 will turn on, causing line 115 to go low and the output of buffer 504 to go low, thus forcing the output from gate 508 to go high. Thus, no matter what the polarity of the amplifier output may be, gate 508 produces a high output.

FIGS. 3a and 3b illustrate a portion of the circuitry used in the ERT detect network 24 in the functional block diagram of FIG. 1. These two circuits monitor the battery voltage and produce logic signal outputs for use by the remainder of the ERT detect circuitry, yet to be described. The terminals 158 and 160 in FIG. 3a are adapted to be connected respectively to the positive bus 50 and the negative bus 52 in FIG. 2. A voltage divider including a resistor 162 and an adjustable resistor 164 causes a potential to exist at the mid-tap point 166 which is proportional to the battery voltage. This signal is applied to the base electrode of a transistor 168 to thereby control the conductivity state thereof. The potentiometer 164 is set so that when the potential of the battery exceeds the predetermined voltage selected as the ERT halfway point, the transistor 168 will be conductive and the output appearing on line 170 will be relatively "low" in a binary sense. However, when the voltage of the battery drops below the predetermined halfway point voltage, the transistor 168 will be turned off and the binary signal appearing on terminal 170 will go "high".

The circuit of FIG. 3b is substantially identical to that of 3a except that the potentiometer 172 is initially set so that the transistor 174 will be conductive whenever the battery voltage applied between the terminals 176 and 178 exceeds the predetermined ERT voltage. Thus, when the battery voltage drops below the ERT voltage, transistor 174 will be rendered nonconductive and the binary signal appearing on output line 180 will go from a "low" condition of a "high" condition. More will be said about the mode of operation of the level sensing circuit of FIGS. 3a and 3b when the remainder of the ERT detect network 24 is described hereinbelow.

Figure 4A:
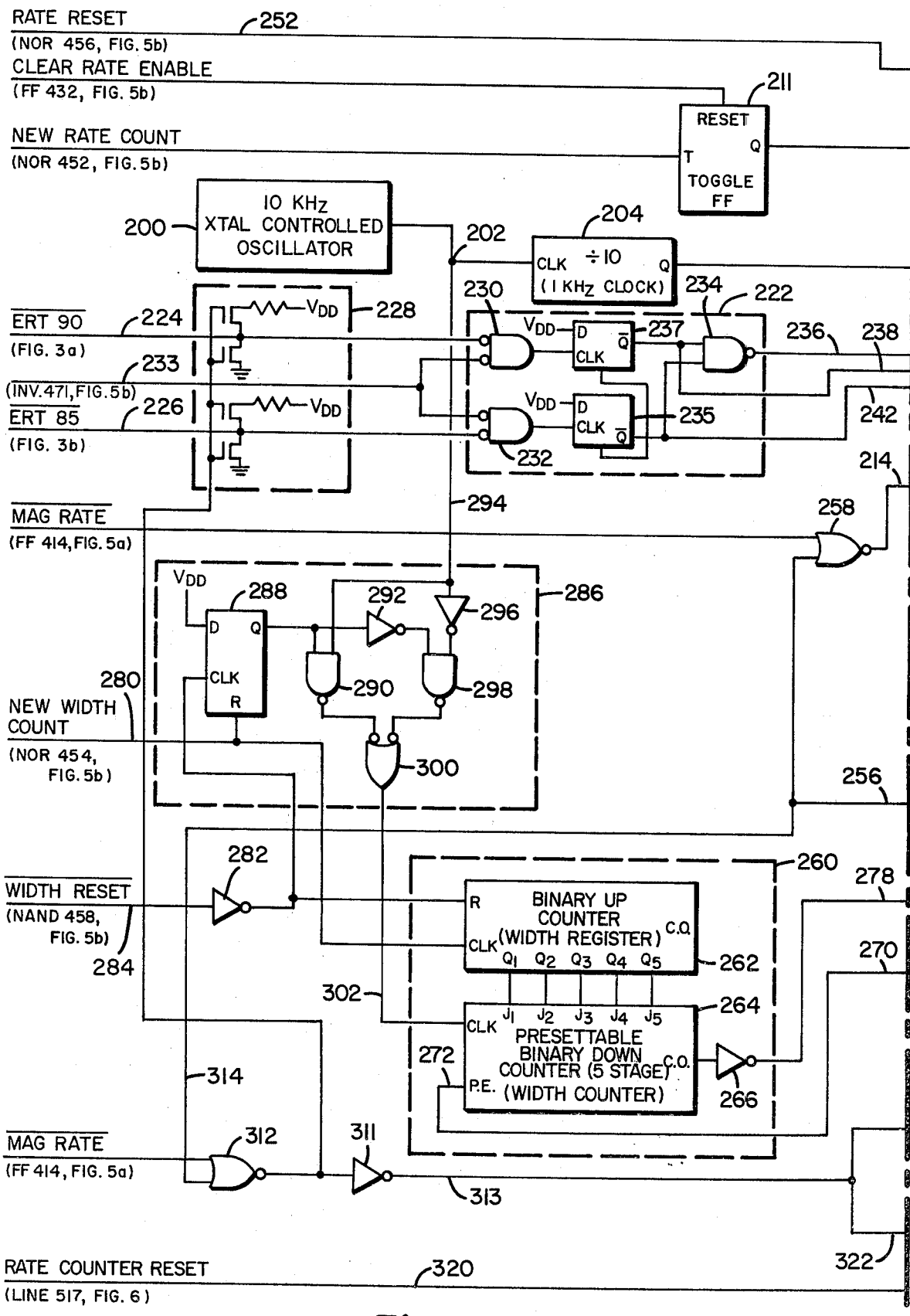
FIGS. 4a and 4b when oriented as indicated in FIG. 4 illustrate the digital logic circuitry for determining the pulse rate and pulse width of the pacer pulses as well as certain additional logic implementing features described in the introductory portion of this specification.
Figure 4B:
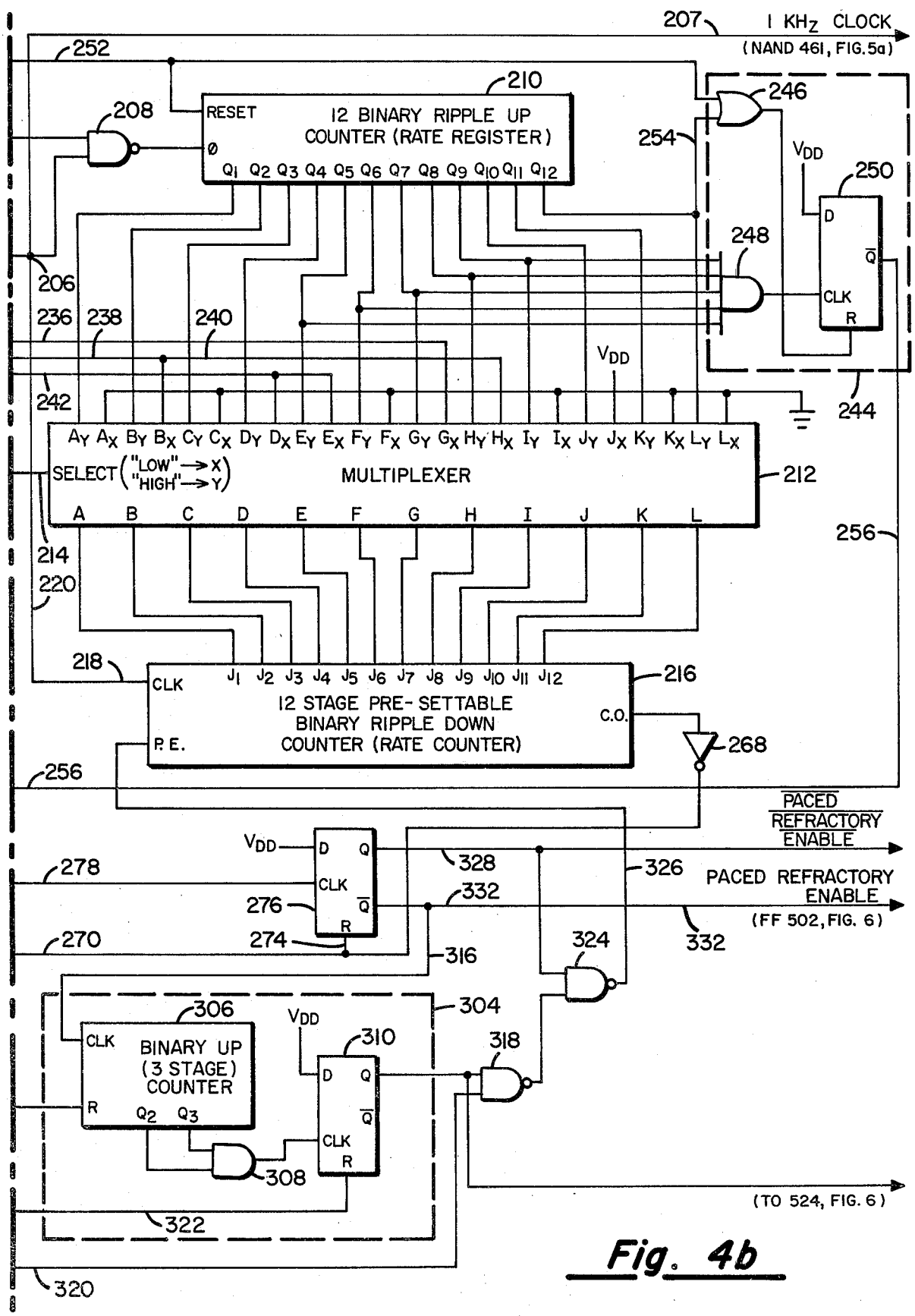

FIGS. 4a and 4b when arranged as shown in FIG. 4 comprise a logic diagram of the Crystal Controlled Oscillator 10, the New Rate Storage unit 12, the New Rate Check circuitry 14, the New Width Storage unit 16, and the Nominal or Mag Rate Select unit 26. Referring to FIG. 4a, a stable square wave oscillator 200 which is crystal controlled, produces pulses at a desired rate, e.g., 10 KHz at its output terminal 202. Connected to the oscillator output terminal 202 is a frequency divider network 204 which operates upon receipt of the leading edges of the pulses from the oscillator 200 to achieve a predetermined frequency division. In the preferred embodiment, the network 204 divides the input frequency by a factor of 10. Thus, for a 10 KHz oscillator output, the output from the frequency divider appearing at junction 206 (FIG. 4b) would be a signal having a pulse repetition rate of 1 KHz. The output from the frequency divider 204 is applied as a first input to a NAND gate 208 whose second input is obtained from the Q output of a toggle flip-flop 211. The output from the NAND gate 208 is coupled to the input terminal of a 12-stage, binary, ripple-up counter 210 which is advanced on the trailing edge of the input signals applied thereto. The binary counter 210 comprises the New Rate Storage device 12 shown functionally in the block diagram of FIG. 1. The true output terminal from the 12 stages of the counter 210 are labeled, respectively, $Q_1$ through $Q_{12}$ and are individually connected to the Y-input terminals of a multiplexer or selector network 212. The selector 212 corresponds to the "Nominal or Mag Rate Select" unit 26 in FIG. 1. In addition to the Y-input terminals labeled $A_Y, B_Y \ldots L_Y$, the multiplexer 212 also has a plurality of X-input terminals labeled $A_X, B_X, \ldots L_X$. Whenever the input applied to the select input terminal 214 is low, the input data appearing on the X-input terminals will be transferred to the corresponding output terminals, i.e., signal on line $A_X$ will be transferred to the A-output terminal, the signal on the input terminal $B_X$ will be transferred to the B-output terminal, etc. Similarly, when the input signal on the select terminal 214 is high, the signals appearing on the input terminals $A_Y, B_Y$, etc., will be transferred to the output terminals A, B, etc.

As shown in FIG. 4b, the output terminals of the multiplexer 212 are coupled to the input terminals labeled $J_1$ through $J_{12}$ of a 12-stage, pre-settable, binary, ripple-down counter 216. The clock input terminal 218 of the ripple-down counter 216 is connected by a conductor 220 to the output of the frequency divider 204 at junction point 206. Hence, the counter 216 will be decremented at a 1 millisecond rate.

The logic circuit shown enclosed by the dashed line box 222 along with the ERT sensing transistor circuits of FIGS. 3a and 3b comprise the major portion of the "Elective Replacement Time Indicator". Output line 170 of FIG. 3a is connected to the input line 224 and the output line 180 of FIG. 3b is connected to the input line 226. A FET switching mechanism indicated generally by box 228 is adapted to connect the input lines 224 and 226 to the logic network 222.

Specifically, the input line 224 will be connected through the FET switch to a first input of a negative AND gate 230 while the input line 226 will be connected through the FET switch to the input of a negative AND gate 232. The second input to each of the gates 230 and 232 comes by way of a conductor 233 from the second stage of a 12-stage binary upcounter 462 in FIG. 5a by way of inverter 471 in FIG. 5b. The output from the negative AND gate 232 is applied to the clock input terminal of a D-type flip-flop 235. Similarly, the output from the negative AND gate 230 is applied to the clock input terminal of D-type flip-flop 237. The $\overline{Q}$ output of the flip-flop 235 serves as a first input to a NAND gate 234. The $\overline{Q}$ output from the flip-flop 237 is applied as the other input to NAND gate 234.

A conductor 236 connects the output from NAND gate 234 to the input terminal $G_X$ of the multiplexer 212. Conductors 238 and 240 connect the output from the flip-flop 237 to the input terminals $B_X$ and $H_X$ of the multiplexer 212. Finally, conductor 242 connects the output from flip-flop 235 to the input terminals $D_X$ and $E_X$ of the multiplexer 212. It is to be noted that terminals $A_X, C_X, F_X, I_X, K_X,$ and $L_X$ are wired to ground and thus continually carry binary "low" signals.

The circuitry for accomplishing the "New Rate Check" represented by Block 14 in FIG. 1 is shown as being enclosed by the dashed line box 244 (FIG. 4b). It includes an OR gate 246 and AND gate 248 and a D-type flip-flop 250, the latter being a leading edge-triggered device. The OR circuit 246 receives as its input a "Rate Reset" signal on conductor 252 and the output from the highest order stage of the counter 210. Specifically, stage $Q_{12}$ of counter 210 is connected by a conductor 254 to the second input terminal of the OR gate 246. The AND gate 248 receives as its inputs the true output from stages 5 through 9 of the 12-stage ripple-up counter 210. The output from AND gate 248 is applied to the "clock" input terminal of a D-type flip-flop 250. The output from the OR gate 246 is connected to the "reset" input terminal of the D-type flip-flop 250. A conductor 256 connects the complement output ($\overline{Q}$) to a first input terminal of a NOR gate 258 (FIG. 4a). The second input to NOR gate 258 connects to the $\overline{\text{Mag Rate}}$ out of the flip-flop 414 shown in FIG. 5a. It is the output of gate 258 which determines whether the X or Y inputs to the multiplexer 212 will be applied to the input lines $J_1$ through $J_{12}$ of the ripple-down counter 216.

The circuitry for determining the pulse width of the stimulating pulses applied to the heart is determined primarily by the circuitry enclosed by dashed line box 260. Included are a binary up-counter 262, a presettable down-counter 264 and an inverter 266. The counter 262 has its output lines $Q_1$ through $Q_5$ connected to the respective input terminals $J_1$ through $J_5$ of the width counter 264. The counter 262 and the counter 264 are each five stages and the count overflow terminal of counter 264 is connected as an input to inverter 266. The "counter over-flow" terminal (C.O.) of the rate counter 216 is coupled through an inverter 268 and is applied via conductor 270 to the "preset enable" terminal (P.E.) 272 of the 5-stage counter 264. The output from inverter 268 is also coupled by a conductor 274 to the "Reset" terminal of a D-type flip-flop 276. The output from the inverter 266 is applied by way of conductor 278 to the Clock input terminal of D-type flip-flop 276.

Signals comprising a new width count are applied by way of input line 280 to the Clock input terminal of the binary up-counter 262 which serves as the width register. As will be explained more fully hereinbelow, the new width count is obtained at the output of negative AND circuit 454 shown in FIG. 5b. The width register 262 is reset by the output from an Inverter 282. Inverter 282 receives as its input a $\overline{\text{Width Reset}}$ signal on line 284 originating at the output of the NAND gate 458 in FIG. 5b.

In order to insure at least a given minimum width to the pacer pulses in the event that the newly programmed width count is erroneously entered, the network shown enclosed by dashed line box 286 is provided. Included are a D-type flip-flop 288 whose Reset input terminal is connected to the input conductor 280 and whose Clock input is connected to the output of inverter 282. The true output terminal, Q, of flip-flop 288 is connected to a first input of a NAND gate 290 and of an inverter 292. The second input to NAND gate 290 comes directly from the output of the 10 KHz oscillator by way of conductor 294. This same 10 KHz signal on conductor 294 is inverted by network 296 and applied to a first input terminal of a NAND gate 298. The second input to NAND gate 298 comes from the output of inverter 292. The outputs from gates 290 and 298 are logically combined in a negative OR gate 300 whose output is connected by way of conductor 302 to the Clock input terminal of the width counter 264. The combination of logic components 290, 292, 296, 298 and 300 merely provide the Exclusive OR function on the output signals from the master clock 200 and the flip-flop 288. Hence, this circuitry can be replaced with a conventional Exclusive OR device.

In order to test the unit after a new rate or pulse width is entered, additional circuitry is provided to permit six cycles of paced pulse generation even in the presence of normal heart activity. This test circuitry is shown as enclosed by dashed line box 304 (FIG. 4b). Included are a three stage binary counter 306, an AND gate 308 and a D-type flip-flop 310. The reset terminal of the counter 306 is connected to the output of a NOR gate 312 (FIG. 4a) by way of inverter 311 and conductor 313. A first input to this last mentioned gate comes from the outut of flip-flop 414 in FIG. 5a and carries the signal $\overline{\text{Mag Rate}}$. The second input to NOR gate 312 is applied by way of conductor 314 and originates at the complementary output terminal, $\overline{Q}$, of the D-type flip-flop 250. The Clock input terminal of counter 306 comes from the complementary output terminal $\overline{Q}$ of the D-type flip-flop 276 by way of a conductor 316. The true output terminals of stages 2 and 3 of the counter 306 are applied as inputs to the AND gate 308 and the output terminal of gate 308 is connected to the Clock input terminal of the D-type flip-flop 310. The flip-flop 310 is triggered on the leading edge of the input clock pulse. The true output terminal, Q, of flip-flop 310 is connected to a first input of NAND gate 318. The second input to this last mentioned gate is applied by way of conductor 320 which comprises the Refractory Reset signal originating at the output of flip-flop 568 in FIG. 6. The output from inverter 311 (FIG. 4a) is connected by conductors 313 and 322 to the reset terminal of the D-type flip-flop 310. The Q output of flip-flop 310 is also coupled to NAND gate 524 (FIG. 6). The output from NAND gate 318 is connected as a first input to a further NAND gate 324. The second input to NAND gate 324 originates at the Q output terminal of the D-type flip-flop 276. The output from NAND gate 324 is applied by way of conductor 326 to the preset enable (P.E.) terminal of the rate counter 216.

The $\overline{Q}$ output from D-type flip-flop 276 is also connected by a conductor 332 to a first terminal of NAND gate 330 (FIG. 6). The complementary output, Q, from D-type flip-flop 276 is also applied by way of conductor 332 to the trigger input terminal of a negative edge triggered, non-retriggerable, monostable multivibrator 336 (FIG. 6). The output from the one-shot circuit 336 is applied as a second input to NAND gate 330. It is the ouput from the NAND gate 330 (FIG. 6) which serves as the "Pacer Rate" input to the voltage doubler circuit of FIG. 2.

Next to be described is the digital logic networks comprising the digital combination lock 18 in the functional block diagram of FIG. 1. This explanation will be facilitated by reference to the logic diagram of FIGS. 5a and 5b.

There is shown at 400 a magnetic reed type switch of the single-pole double-throw type. This switch controls the state of a bistable flip-flop 402 which includes the crosscoupled OR inverters 404 and 406. The flip-flop 402 acts in a conventional fashion to eliminate the effects of contact bounce occurring upon operation of the magnetic reed switch 400. The output from the "set" side of the flip-flop 402 is connected by conductor 408 to the Clock input terminal of a threestage input pulse counter 410. It is also connected by a conductor 412 to the Reset terminal of a D-type flip-flop 414. A set of four negative AND gates 416, 418, 420 and 422 are provided for translating the true and inverted versions of the output signals from the binary counter 410. More speecifically, the output from stage $Q_1$ of counter 410 is applied as an input directly to gates 420 and 422 while the inverted version thereof is applied as an input of the gates 416 and 418. Similarly, the output from stage $Q_2$ of counter 410 is connected directly to an input of gates 416 and 420 and through an inverter to the inputs of gates 418 and 422. Finally, the true output $Q_3$ from the counter 410 is connected directly to an input of gates 418 and 422 and through an inverter to the inputs of gates 416 and 420. The respective output lines from gates 416 through 422 are applied as inputs to an OR gate 424, the output of which is coupled by a conductor 426 to the reset side of a flip-flop 425. The output from the flip-flop 425 is connected to an OR gate 427 whose output is then connected to the Reset input terminal of the binary up-counter 410 by means of a conductor 429. The output from the gates 416, 418, 420 and 422 are also individually connected to a Clock input terminal of a corresponding set of D-type flip-flops 428, 430, 432 and 434. The Reset terminals of each of these last-mentioned flip-flops are connected by a conductor 436 to the Q output terminal of the D-type flip-flop 414. It is to be further noted that the true output terminal, Q, of flip-flop 428 is connected by a conductor 438 to the "Data" input terminal (D) of the flip-flop 430, and likewise, the true output terminal, Q, of flip-flop 430 is connected to the D input terminals of the flip-flops 432 and 434. A D-type flip-flop, herein termed the "Pulse Code Sample Flip-Flop" 448 is provided and when set, provides an enabling signal, via conductor 450, to the gates 416, 418, 420 and 422. The conditions under which flip-flop 448 will be set will be presented later in this specification.

A further set of three negative AND gates 452, 454, 456 and a NAND gate 458 is also included in the combination lock circuitry. Negative AND gate 452 receives as its input, the complementary output, Q, of the flip-flops 428, 430 and 432. In addition, the output from the NOR gate 406 of the flip-flop 402 is applied by way of a conductor 460 to an additional input terminal of the gate 452. Negative AND gate 454 receives as its input the complementary output, Q, from flip-flops 428, 430 and 434 as well as the output from the set side of fli-flop 402. Gate 456 has as its inputs the Q output from flip-flop 430 and the output from gate 420 via inverter 421. Finally, NAND gate 458 receives as its inputs the true output from the flip-flop 430 as well as the output from the negative AND gate 422.

The output from negative AND gate 452 comprises the input signal "New Rate Count" applied to the toggle input terminal (T) of flip-flop 211 (FIG. 4a). The output from gate 454 comprises the input signal "New Width Count" applied to the input line 280 (FIG. 4a). The output from gate 456 is the "Rate Reset" applied to the input line 252 in FIG. 4a and the output from NAND 458 comprises the signal width Reset applied to the input line 284 in FIG. 4a. The complementary output from the flip-flop 432 comprises the input signal "Clear Rate Enable" applied to the Reset input terminal of the toggle flip-flop 211 in FIG. 4a.

The complementary output terminal, Q, of flip-flop 414 is applied as a first input to a NAND gate 461. The second input to this last mentioned NAND gate comes from the output of the frequency divider 204 in FIG. 4a and the output from the NAND gate 461 is applied to the count input terminal, $\phi$, of a 12-stage, binary, ripple-up counter 462. The true output from stages $Q_5$, $Q_7$, $Q_8$ and $Q_{12}$ of the counter 462 are combined in AND circuit 464 and the output thereof is applied by a conductor 466 to the Clock input terminal of the D-type flip-flop 414 and the D input of a flip-flop 467. The flip-flop 467 has its Clock input terminal connected to the output of the frequency divider 204 and is therefore energized at a 1 KHz rate. The output from flip-flop 467 is connected to the Reset terminal of the counter 462. The output from stage $Q_6$ of the counter 462 is applied by way of an inverter 468 to the Clock input terminal of the D-type flip-flop 448. This flip-flop is adapted to be reset by the output from the NAND gate 461. The signal "Mag Rate" applied to the NOR gate 312 in FIG. 4a comes from the true output, Q, of the D-type flip flop 414. The output stage $Q_2$ of the program interval 30 counter 462 is connected by a conductor 469, an inverter 471 and a conductor 233 to the input terminals of the negative AND gates 230 and 232 in FIG. 4a. The outputs from stages $Q_5$, $Q_7$ and $Q_8$ are combined in AND gate 473 and the resulting logic signal output therefrom is applied to the clock input terminal of a D-type flip-flop 475. The Reset terminal of this last-mentioned flip-flop is connected to the Q output terminal of the flip-flop 414. The Q output terminal of flip-flop 475 is connected to the OR gates 427. The complementary output, $\overline{Q}$, of flip-flop 475 is connected to the D-input of the Pulse Code Sample flip-flop 448.

This completes a description of the circuits for implementing the digital combination lock network. Next to be described will be the construction of the refractory Generator 42 and the Noise Detect network 44 illustrated in the functional block diagram of FIG. 1. This will be accomplished with the aid of FIG. 6, which shows by means of a digital logic diagram, the structure implementing same.

Shown in FIG. 6 are first and second flip-flops 500 and 502. The flip-flop 500 may be referred to as the "Sense Refractory Flip-Flop" while the flip-flop 502 may be referred to as the "Paced Refractory Flip-flop." As was mentioned earlier in this specification, the cardiac pacer of the present invention has a dual refractory system incorporated in it. A 256 millisecond refractory period is provided following a naturally occurring heartbeat whereas a 320 millisecond refractory period is established for a heartbeat resulting from the application of a pacer pulse. It will be recalled that a signal is produced on line 114 or line 115 (FIG. 2) whenever the heart is producing a natural electrical output, upon contraction, which exceeds a given threshold in the absence of extraneous noise. These signals are applied by way of buffer amplifiers 504 and 506 to the inputs of a NAND gate 508. The output from NAND gate 508 connected to the Clock input terminal of the Sensed Refractory Flip-Flop 500. The Paced Refractory Flip-Flop 502 has the "Paced Refractory Enable" signal from the Q output terminal of flip-flop 276 (FIG. 4b) applied to its Clock input terminal. The complementary output, Q, of flip-flop 502 is connected to the data input terminal of the flip-flop 500. The complementary output signals from both flip-flops 500 and 502 are applied as inputs to a NAND gate 512. The output from this gate is connected to the D input terminal of a noise flip-flop 514. It is also applied by way of an inverter 516 to the reset input terminal of the noise flip-flop 514.

The output from NAND gate 508 is also connected by a conductor 518 to a first input terminal of an AND gate 520. The output from this last-mentioned gate is applied to the clock input terminal of the D-type flip-flop 514. The output of AND gate 520 is also connected to an input of a NAND gate 522. A second input to gate 522 comes from the Q output terminal of the noise flip-flop 514. NAND gate 522 has its output connected first to one input of a four-input NAND gate 524; a second input to this gate comes from the output of flip-flop 310 (FIG. 4b) and another input comes from the flip-flop 414 in FIG. 5a which is the "$\overline{\text{Mag Rate}}$" signal. The final input to the NAND gate 524 comes from the output of the NAND gate 512.

The output from NAND gate 524 is connected to the reset terminal of a nine-stage binary up/down counter 526 which is referred to herein as the "Refractory Interval Counter." This counter is advanced by pulses appearing on the input line 528, each time that the NAND gate 530 is enabled. Gate 530 has two inputs, one being connected to the output from NAND gate 512 and the other coming from the ouput of the frequency divider 204 in FIG. 4a by way of line 207.

In this particular application, the signals appearing only at the output of stages 7, 8 and 9 of the counter 526 are of interest. The output from stage $Q_7$ is applied to a number of gates. Specifically, gate 532 has a first input connected to state $Q_7$ and a second input connected to the output from stage $Q_9$ of the counter 526. The stage $Q_7$ output is also connected as an input to a NAND gate 534 whose output is coupled by a conductor 536 to a first input of negative OR circuit 538. The output of the negative OR circuit 538 is connected to the reset terminal of the Sensed Refractory Flip-Flop 500. The output from NAND gate 534 is also coupled through negative OR circuit 540 to the reset terminal of the Paced Refractory Flip-Flop 502 by way of a conductor 542. The second input to OR gate 540 is provided by the output from the NAND gate 532. The second input for the negative OR circuit 538 comes from stage 9 of the counter 526 by way of an inverter 544. The output from stage $Q_7$ of counter 526 is applied to an AND gate 546 along with the output from stage $Q_8$ of the counter. The output from gate 546 is connected by conductor 548 to the reset terminal of a D-type flip-flop 550. The clock input terminal of this flip-flop 550 is connected by conductors 552 and 554 to the output from the flip-flop 276 (FIG. 4) which provides the "Paced Refractory Enable."

A signal from the Q output terminal of flip-flop 500 is logically combined with the output from AND circuit 546 in the NAND gate 556. The output from NAND gate 556 is applied as a first input to a still further NAND gate 558 whose other input is connected to the output of the inverter 544. The output from gate 558 is connected to the reset terminal of a D-type flip-flop 560. The complementary output from the flip-flop 560 is connected by way of conductor 562 to a second input terminal of the AND circuit 520.

The output from NAND gate 522 is connected to a Clock input terminal of a D-type flip-flop 564. The Q output terminal of flip-flop 564 is applied as a second input to the NAND gate 534. The reset terminal of flip-flop 564 is connected to the output from the inverter 516.

A pair of additional D-type flip-flops 566 and 568 along with a NAND gate 570 are also included in the dual refractory period network circuitry. The clock input terminal of flip-flop 566 is connected to the Q output terminal of the flip-flop 500. The Q output terminal of flip-flop 566 is connected to the Data (D) input terminal of the flip-flop 568. The clock terminal of flip-flop 568 is connected by way of a conductor 572 to the 10 KHz clock line which connects to oscillator 200 in FIG. 4a. The Q output terminal of flip-flop 568 is connected to the reset terminal of the flip-flop 566. The signal emanating from the Q output terminal of flip-flop 568 is the "Rate Counter Reset" signal utilized by the circuitry of FIG. 4a.

This completes a description of the construction of the preferred embodiment of the invention. To follow will be a discussion of its operation in its various modes.

OPERATION

Faced Mode With Programmed Rate

When operating in the paced mode with a programmed rate the following initial conditions apply:

1. The binary counter 210 (FIG. 4b) contains a count which corresponds to the programmed rate interval.
2. The flip-flop 250 is set and the $\overline{\text{Magnetic Rate}}$ line (FIG. 5b) is low.

Under the assumed conditions gate 258 is fully enabled and produces a high output signal to the input select line 214 of the multiplexer 212. As is indicated by the legend on the drawing, this selects the Y inputs of the multiplexer 212 such that each of the $Q_1$ through $Q_{12}$ outputs from the binary register 210 are presented as the $J_1$ through $J_{12}$ inputs to the binary rate counter 216.

Starting with a high pulse from the NAND gate 324 (FIG. 4b), the preset enable input (P.E.) or the rate counter 216 is high causing the count from the rate register 210 to be entered into the rate counter 216. The 1 KHz clock signals emanating from the frequency divider 204 are applied to the clock input terminal 218 of the rate counter 216 such that at each 1 millisecond interval, the counter 216 is decremented until it reaches zero. Then, on the next clock pulse, the counter 216 reverts to its all 1's state. This causes the carry output (C.O.) signal to go low. This low signal is inverted by circuit 268 such that the signal on conductor 270 is high. The high signal is applied to the "Reset" terminal of flip-flop 276 by means of conductor 274 and the flip-flop 276 is thereby reset. This results in the removal of the preset enable from the counter 216 (by way of gate 324) which causes the output from the inverter 268 to return to its low state.

The preset enable applied to the width counter 264 causes the contents of the width register 262 to be transferred into the width counter 264. The 10 KHz pulses occurring at the output from the crystal controlled oscillator 200 are applied by way of conductor 294 and through the minimum width control logic, shown enclosed by dashed line box 286, such that 0.1 millisecond clock pulses are applied by way of conductor 302 to the width counter 264. These clock pulses cause the count in counter 264 to be decremented until, upon reaching all 1's state, the carry output terminal (C.O.) goes low. This low signal is inverted by circuit 266 causing a high clock signal to be applied to the flip-flop 276 by way of conductor 278. The clock signal applied to the flip-flop 276 returns it to its "set" state. it can be seen, then, that a pulse whose width has been determined by the contents of the width register 262 has been generated at the Q output terminal of the flip-flop 276 at a rate determined by the contents of the rate register 210. This pulse from the flip-flop 276 passes through the gate 330 (FIG. 6) to generate the "Pacer Rate" signal.

The Pacer Rate signal from the gate 330 is coupled through the resistor 58 (FIG. 2) to turn on transistors 60 and 64. With transistor 64 conducting, the potential at its collector drops and the transistor 78 is also turned on. With transistor 78 conducting, a pulse approximately equal to the sum of the battery voltage plus the voltage across the capacitor 82 is applied to the heart electrode terminals 70 and 74 and to the heart of the patient via implanted electrodes (not shown).

Paced Mode With Magnetic Rate

When a permanent magnet is placed in proximity to the implanted pacer, the reed switch 400 (FIG. 5) closes, causing an "0" signal to be applied at the input of NOR circuit 404 of the flip-flop 402. This results in a setting of the flip-flop 402 and the logical 37 1" output from gate 404, when applied by way of conductor 412 causes the flip-flop 414 to be reset, causing the "$\overline{\text{Magnetic Rate}}$" line (FIG. 5b) to go high. This, in turn, causes the output of the NOR gate 258 (FIG. 4a) to assume a low state which has the effect of selecting the X inputs of the multiplexer 212. Thus, the pulse rate will now be determined by the combined outputs of the gate 234 and flip-flops 235 and 237. That is, rather than having the contents of the binary counter 210 transferred to the Rate Counter 216 as was the situation in the "Paced Mode With Programmed Rate" described above, the new rate will be a function of the logic circuits enclosed by dashed line box 222 along with the prewired low inputs of the multiplexer 212.

The placing of the permanent magnet in proximity to the pacer also causes the output of gate 312 (FIG. 4a) to go low. The P channel FET's (in box 228) which are normally off to conserve power now turn on while the N channel FPET's turn off. Resistor 164 (FIG. 3a) is adjusted such that transistor 168 will be at the threshold of conduction when the battery is at the predetermined voltage selected as the ERT halfway point (e.g., 2.3 volts). Thus for a battery voltage above this value, line 170 will remain low while for a battery voltage below this halfway point, it will go high. Transistor 174 is similarly set at the predetermined ERT value (e.g., 1.8 volts). After the Magnetic Rate Mode has been initiated, a 2 millisecond delay allows time for lines 170 and 180 to settle to their correct state. Subsequently, the $Q_2$ output of counter 462 (FIG. 5a) goes high causing the output of inverter 471 to go low. This results in flip-flop 237 being clocked to the set state, if transistor 168 is conducting and also causing flip-flop 235 to be clocked to the set state, if transistor 174 is conducting.

Let it first be assumed that the battery voltage is at its beginning of life (BOL) value. Under this assumed condition, the ERT 90 line 224 and the ERT 85 line 226 (lines 170 and 180 in FIGS. 3a and 3b) are both low. Thus, the $\overline{Q}$ output of flip-flop 235 will be high (a binary 1), the $\overline{Q}$ output of flip-flop 237 will be low (a binary 0) and the output of gate 234 will be high (a binary 1). It can be seen that this causes the X inputs to the multiplexer 212 to assume the binary state 001001011000 ($600_{10}$). (The A input is the least significant bit.) This corresponds to an interval of 600 milliseconds and, hence, the pacer rate will be 100 beats per minute.

As the battery discharges during its life and falls halfway to the elective replacement time (ERT) value, transistor 168 (FIG. 3a) becomes nonconducting, causing the ERT 90 line to go high. The $\overline{Q}$ output of flip-flop 235 will now be a 1, the $\overline{Q}$ output of flip-flop 237 will be a 1 and the output of gate 234 will be a 0. This generates a binary count of 001010011010 ($666_{10}$) at the X inputs of the multiplexer 212. This number corresponds to a 666 millisecond interval or 90 beats per minute pacer rate.

As the battery voltage decays lower and falls to the ERT voltage, both transistors 168 and 174 in FIGS. 3a and 3b will be nonconducting and both the ERT 90 and ERT 85 lines 224 and 226 assume a high condition. Under these circumstances, the $\overline{Q}$ output from flip-flop 235 is a zero, the $\overline{Q}$ output of flip-flop 237 is a 1 and the output of gate 234 is a 1, generating a binary count of 001011000010 ($706_{10}$). This corresponds to an interval of 706 milliseconds or 85 beats per minute. Thus, it can be seen that the condition of the battery can be inferred by monitoring the pacer rate when the system is in its magnetic mode. Note that flip-flops 235 and 237 cannot be reset while in the Magnetic Rate Mode. This feature eliminates the possibility of erratic fluctuations in rate when either of transistors 168 or 174 are exactly at the conduction threshold.

Refractory Timing Generation

FIG. 6 contains all of the circuitry associated with the generation of the refractory interval for the pacer of the present invention. The refractory intervals are controlled by the 9-stage, binary, ripple-up counter 526. In the normal mode, it will be recalled that the $\overline{\text{Magnetic Rate}}$ line is high. Also, the flip-flops 500 and 502 and the counter 526 are initially reset. If a normal heart signal is picked up at the heart electrode terminals 70 and 74 (FIG. 3) it will be amplified, filtered and level detected by the circuitry of FIG. 2 and if the amplitude of the electrical signal from the heart exceeds the requisite threshold, the transistor 101 and 103 (FIG. 2) will be turned on. This will cause a positive or negative pulse to be produced at the output of the buffer amplifier 504 or inverter 506 (FIG. 6) which clocks the flip-flop 500 into its "set" condition. The positive going edge of the Q output from the flip-flop 500 clocks the flip-flop 556 to the set state. The next leading edge of the 10 KHz clock sets flip-flop 568 which resets flip-flop 566 causing a reset of flip-flop 568 on the next clock cycle. Thus, a 0.1 millisecond positive going Rate Counter Reset pulse is generated on line 517. This pulse is applied by way of line 320 (FIG. 4a) to an input of gate 318 (FIG. 4b). The output of gate 318 will therefore go low, causing the gate 324 to produce a high output signal, which acts as a preset enable for the Rate Counter 216 and allows the contents of the Rate Register 210 to be re-entered into the Rate Counter 216. At the same time, NAND gate 512 (FIG. 6) produces a high output signal which, when applied to an input of the NAND gate 524 causes the output of this last-mentioned gate to go low, thereby releasing the reset on the Refractory Interval Counter 526.

The output from gate 512 also enables gate 530 such that the 1 KHz clock signal can be propagated to the counter input terminal 528. Upon each trailing edge of a clock signal applied to the counter input terminal 528, the contents of the counter will be incremented until the output $Q_9$ (the highest order stage) assumes its 1 state. When this happens, the signal applied by way of inverter 544 and gate 538 to the reset input terminal of the flip-flop 500 causes the flip-flop 500 to be reset. This causes the NAND gate 512 to output a low signal and the gate 524 to output a high signal which resets the Refractory Interval Counter 526 to a value of zero. With a 1 KHz clock rate, it will take 256 milliseconds for stage 9 of the counter to become a binary 1. This corresponds to the basic 256 millisecond refractory period associated with a sensed natural heart beat. During this time, additional heart output signal picked up by the electrodes 70 and 74 are inhibited from generating a rate counter reset pulse. As long as there is a sensed natural heart signal following the refractory period which generates a rate counter reset prior to the countdown of counter 216 (FIG. 4b), the device will run in this normal sensed mode with a 256 millisecond refractory period. Whenever a natural heart signal is missing such that the rate counter reset is not generated, the counter 216 will complete its countdown, which generates a Pacer Pulse and a Paced Refractory Enable which clocks the flip-flop 502 to its set condition. The complementary output, $\overline{Q}$, of the flip-flop 502 causes a low or zero signal to be applied to the data terminal, D, of flip-flop 500, thereby preventing it from being set. In this manner, the state of flip-flop 502 now controls the refractory period. The pacer pulse also sets flip-flop 550 causing transistor 100 to turn on and Differential Bandpass Amplifier 87 to be switched to a zero gain state. As such, currents flow to charge capacitors 86, 107 and 108 to hold the bases of transistors 101 and 103 at their quiescent level independent of any input signals. In this mode, the Amplifier 87 can rapidly recover from large noise pulses induced by a pacer pulse when transistor 100 is turned off. Amplifier 87 assumes a high gain state and input signals then will cause excursions from this fixed quiescent level. By incorporating this controlled gain feature, problems related to amplifier recovery following a natural heart signal are minimized.

As was true before, the output from NAND gate 512 goes high, causing the counter 526 to begin counting clock pulses arriving at a 1 KHz rate via gate 530. At a count of 192, AND gate 546 goes high which resets flip-flop 550 thus restoring Amplifier 87 to its normal gain. This time, when the count reaches $256_{10}$, the signal applied to the reset terminal of flip-flop 500 has no effect since it was never set. Counting therefore proceeds to a binary count of 101000000 which corresponds to a $320_{10}$ millisecond interval. When the aforementioned count is reached, the gate 532 will be fully enabled and will produce an output signal that passes through gate 540 and on line 542 which resets the flip-flop 502. The D input of the flip-flop 500 now assumes a "1" state and any subsequent natural heart signals will generate a refractory reset. Thus it can be seen that a 320 millisecond refractory period is established after the occurrence of a paced heart beat.

Noise Detection

The noise detection circuitry operates to assures that the rate counter will only be reset on a sensed heartbeat and not on spurious noise. When a Paced Refractory period is initiated by setting flip-flop 502, the output of the inverter 516 goes low, releasing the reset on flip-flop 514 and 564. Flip-flop 560 is also set by the negative going pacer pulse applied to the input of NAND gate 570. With the $\overline{Q}$ output of flip-flop 560 low, noise pulses are inhibited by AND gate 520. Two hundred and fifty-six milliseconds into the refractory period, stage $Q_9$ of the refractory interval counter 526 sets, causing the output of inverter 544 to go low and the output of NAND gate 558 to go high, thus resetting flip-flop 560. A subsequent noise pulse will now propagate through AND gate 520 setting flip-flop 514 and causing the output of NAND gate 522 to go low, thus resetting counter 526 via NAND gate 524. On the trailing edge of the noise pulse the output of NAND gate 522 goes high, setting flip-flop 564 and thus enabling NAND gate 534. If counter 526 reaches a count of $64_{10}$, NAND gate 534 goes high, generating a reset of flip-flop 502 via gate 538. However, another noise pulse will reset counter 526 and thus extend the refractory period an additional 64 milliseconds.

When flip-flop 502 is reset, flip-flops 514 and 564 are also reset via NAND gate 512 and inverter 516. Should the noise condition persist, the rate counter 216 will eventually count down through zero and generate a pacer pulse. The noise detection circuits function in the same manner in the "sensed mode" except that noise detection is started earlier in the refractory period. The $\overline{Q}$ output from flip-flop 568 sets flip-flop 560 via NAND gate 570 so, as before, noise pulses are initially inhibited. With flip-flop 500 set NAND gate 556 is enabled thus when $Q_7$ and $Q_9$ of counter 526 go high at a count of $192_{10}$ the output of AND gate 546 goes high causing flip-flop 560 to be reset via NAND gates 556 and 558, thus initiating noise detection of 64 milliseconds earlier than in the "paced mode".

To summarize this section of the specification dealing with the refractory period generation, without rate counter resets, the unit goes into a paced mode with pacer pulses being generated at a rate determined by the contents of the rate register 210. For a rate counter reset to be generated, flip-flop 500 must be reset. Once flip-flop 500 or 502 has been set, it can only be reset through achieving the appropriate count in the refractory interval counter 526. Any noise pulses during the noise detection period will cause the counter 526 to repeatedly reset and to extend the refractory period until a 64 millisecond noise free interval has passed. Furthermore, the "Magnetic Rate" mode causes the counter 526 to be continually reset by virtue of the output from the NAND gate 524.

Combination Lock Circuits

In order to reprogram a new pulse rate into the implanted pacer from an external source, it is first necessary to unlock the combination lock circuitry by presenting to it a predetermined code word. A three digit pulse train has been adopted in the preferred embodiment. In order to effect a change in the pulse rate, a code 5-3-4 must be presented. Similarly, in order to change the pulse width of the pacer signal, the code 5-3-2 must be presented.

Figure 5A:
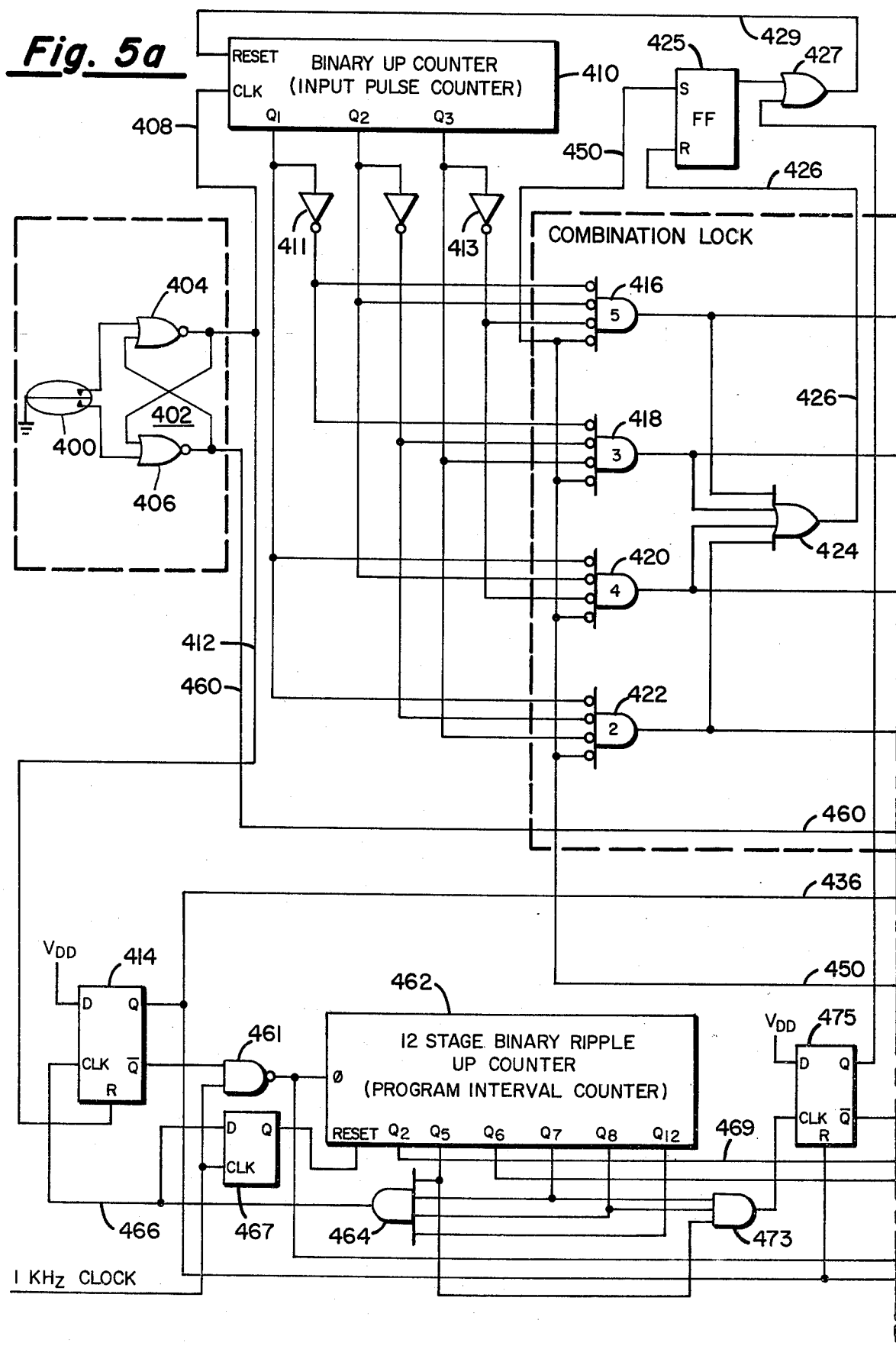
FIGS. 5a and 5b when arranged as shown in FIG. 5 illustrate the logic circuitry for implementing the combination lock feature and certain control circuitry utilized therein.
Figure 5B:
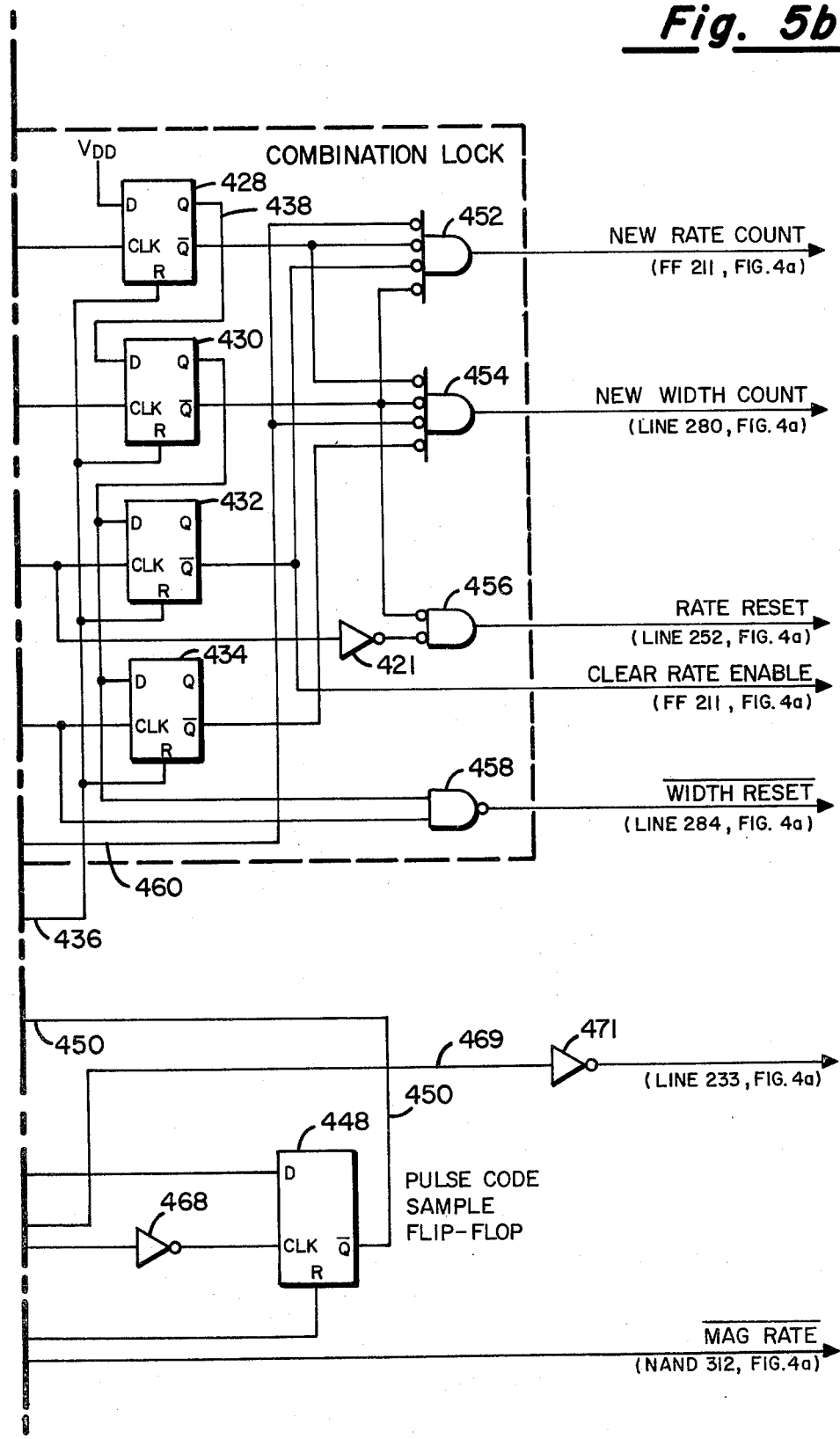

Referring to FIGS. 5a and 5b, initially all of the flip-flops 428 through 434 and the counters 462 and 410 are reset. Flip-flop 414, however, remains set. On the first cycle of the magnetic reed switch 400 caused by the pulsing of an external electromagnet, the output from the set side of the flip-flop 402 goes high which resets the flip-flop 414 via a pulse on conductor 412. This enables the 1 KHz clock signals to propagate through NAND gate 461 and to begin incrementing the Program Interval Counter 462. The flip-flop 414 remains reset throughout the programming interval, causing the pacer to run in the "Magnetic Rate" mode previously described. The external electromagnet positioned in proximity to the implanted pacer operates at a modulation frequency of 100 Hz. Each cycle of the magnetic reed switch 400 causes the input counter 410 to increment. When the program interval counter 462 reaches a count of $64_{10}$, inverter 468 outputs positive going clocking signals for the Pulse Code Sample flip-flop 448. The complementary output, $\overline{Q}$, of flip-flop 448 goes low and then is immediately reset to the high state by the next clock pulse appearing at the output of NAND gate 461. The output from the flip-flop 448 on conductor 450 therefore serves to sample the state of the input pulse counter 410 by enabling the gates 416 through 422. If five pulses have been registered in counter 410 during this first 64 millisecond interval, the count in counter 410 will be $101_2$ and the outputs of inverters 411 and 413 will be low as will the output of stage $Q_2$ of counter 410. With all four inputs of the gate 416 low, its output goes high, causing the output of the OR gate 424 to go high, thus setting flip-flop 425 which then resets counter 410. At the same time, flip-flop 428 is clocked to its "set" state. For any count other than five, the output of gate 416 remains low and counter 410 and flip-flop 428 are unchanged. The counter 410 then accumulates counts during the next sampling interval and 64 milliseconds later, the $\overline{Q}$ output of flip-flop 448 again goes low. If a count of three has been entered into counter 410, the output of gate 418 will go high, clocking flip-flop 430 and also resetting the counter 410 by way of the output from OR circuit 424, flip-flop 425, and OR circuit 427. In a like manner, a count of four will enable gate 420 and a count of two will enable the gate 422.

It should be noted at this point that the output from the flip-flop 428 feeds the flip-flop 430 and the output of flip-flop 430 feeds flip-flop 432 such that flip-flop 430 cannot be set until flip-flop 428 has first been set, and neither flip-flops 432 and 434 can be set until flip-flop 430 has been set. This, then, is the basis for the combination lock feature. In the first 64 millisecond time period, there must be a count of five, in the second such time period there must be a count of 3 and in the third such time period there must be either a count of 4 or 2 to set flip-flops 432 or 434 respectively. Any other pulse pattern is rejected without altering the counters 210 or 262 (FIGS. 4b and 4a). Since the combination lock requires a specifically different count for each of the sampling intervals it is impossible for noise of any single frequency to open the combination. Furthermore, it is very improbable that any random pattern of noise would match the combination.

After three sampling pulses have been presented from the Q output of flip-flop 448, flip-flop 475 gets set causing the D input of flip-flop 448 to go low, thus inhibiting the production of further sampling pulses. Counter 410 is also maintained in a reset condition via gate 427. This assures that gates 416, 418, 420 and 422 will also be inhibited through the remainder of the programming cycle.

For a valid 5-3-4 code, the output from gate 420 goes high causing the inverter 421 to output a low signal. Since flip-flop 430 had previously been set, the output from NOR circuit 456 goes high producing the "Rate Reset" signal which is applied by way of conductor 252 to the Reset input terminal of the Rate Register 210 in FIG. 4b. At the same time, the flip-flop 250, which is the Program Rate Check flip-flop, is reset by the output from OR circuit 246.

When flip-flop 432 assumes its "set" condition, the "Clear Rate Enable" line goes low releasing the reset on the toggle flip-flop 211. The next cycle of the reed switch will cause the output from gate 452 to go high, toggling flip-flop 211 to its "set" state. This allows the 1 KHz clock signal to propagate through gate 208 and begin incrementing the counter 210 at a 1 millisecond rate. This incrementing operation continues until a second cycle of the reed switch 400 generates a second pulse at the output of gate 452 which toggles the flip-flop 211 to the "reset" state and terminates the incrementation of the rate register 210. In this manner, the resulting count in the rate register 210 is determined by the time interval between the first rate count pulse and the second rate count pulse. Use of this gated clock method is considerably faster than counting input pulses. The use of this latter method might require up to one minute to complete the programming function.

If a valid 5-3-2 code is entered by way of the magnetic reed switch 400, then flip-flop 434 is set. At this time, gate 422 is producing a high output, causing the output from NAND gate 458 to go low. This low signal is applied by way of conductor 284 (FIG. 4a) and causes the output from inverter 282 to go high, thereby resetting the Width Register counter 262. The output from inverter 282 is also effective to set the flip-flop 288. For each subsequent programmer pulse, the output of gate 454 goes high, producing the "New Width Count" signal which is applied by way of conductor 280 to the clock input terminal of the Width Register 262. Hence, the contents of the Width Register are incremented each time a programmer pulse causes the output from gate 454 to go high.

In the event that there are no width count signals emanating from negative AND gate 454, the flip-flop 288 (FIG. 4a) will remain in its set condition. Should an excessive number of width counts be applied to the counter 262, it will overflow and automatically recycle to its lowest count and then increment again. The effect of this action is that at the end of the programming operation, flip-flop 288 will be cleared unless counter 262 is in its zero state. With flip-flop 288 set, the gates 290, 292, 296, 298 and 300 cause the phase of the clock input to the counter 264 to be inverted. This has the effect of delaying the time for the counter to change state by ½ clock pulse or 0.05 milliseconds. Thus the circuitry contained in the dashed line box 286 comprises a hard-wired connection assuring at least a minimum width to the pacer pulses. This feature is provided to guard against a failure to enter any width count after successfully addressing the pulse generator.

It should be noticed that for any other code than the 5-3-4 or the 5-3-2 codes, gates 452, 454, 456 or 458 are not enabled and the pre-existing width value and rate value remain unchanged. After a period of 2,256 milliseconds has elapsed following the start of a reprogramming operation, the output from gate 464 goes high which clocks flip-flop 414 to its "set" state thereby inhibiting clock pulses to counter 462. On the next clock pulse, flip-flop 467 sets, resetting counter 462, which causes the output of gate 464 to clear flip-flop 467 on the following clock pulse. The output from the Q side of the flip-flop 414 is applied by way of conductor 436 to the Reset terminals of each of the flip-flops 428, 430, 432, and 434, resetting same and thereby conditioning them, or the combination lock circuitry, for receipt of subsequent reprogramming codes.

Programming Rate Check and Runaway Protect

The "Magnetic Rate" mode enables NOR gate 312 (FIG. 4a) causing the three stage counter 306 to be reset by way of the output from inverter 311 on conductor 313. Similarly the Magnetic Rate signal on line 322 resets the flip-flop 310. This inhbits the "Rate Count Reset" pulse on line 320 from propagating through the NAND gate 318. Hence, the unit is always operating in the paced mode when the magnetic rate mode is operative. After removal of the permanent magnet used to establish the magnetic rate, the counter 306 is incremented each time that flip-flop 276 is clocked. This continues until a binary count of 110 (decimal 6) is reached at which time the output from gate 308 goes high, thus clocking flip-flop 310 to the "set" condition. This allows Rate Counter Reset pulses to propagate on through the gate 318. This feature provides for six paced intervals running at the programmed rate even in the presence of naturally occurring electrical heart activity which is operative to produce refractory resets. When the flip-flop 276 is clocked to its "1" state, the nonretriggerable monostable multivibrator 336 (FIG. 6) is triggered to its active state causing its Q output to go positive for a predetermined time period. Specifically, the output from the one-shot circuit 336 will remain positive, independent of any further input trigger signals, for a period of 462 milliseconds. If during this interval a second pacer pulse is generated, it will be inhibited by the gate 330. Thus, the paced rate can never exceed 130 beats per minute. If a rate in excess of 130 beats per minute is attempted, the monostable multivibrator suppresses every other pulse to thereby halve the output rate.

During rate reprogramming, the flip-flop 250 (FIG. 4b) serves as a check on the rate count. When counter 210 reaches a binary value of 11111000 ($496_{10}$), the output from gate 248 goes high, clocking flip-flop 250 to the "set" state. If the counter runs beyond $2047_{10}$, bit $Q_{12}$ of counter 210 goes high causing flip-flop 250 to reset by way of a pulse from OR gate 246. If at the end of a reprogramming cycle the Q output of flip-flop 250 is high, then counter 306 will be maintained in the reset state by way of NOR gate 312 and inverter 311 and the Mag Rate inputs to multiplexer 212 will be selected by way of NOR gate 258. The pacer will therefore run in the "Paced Magnetic Rate" mode, unless the rate count is between $496_{10}$ and $2047_{10}$. This corresponds to a programmed rate between 30 beats per minute and 120 beats per minute.

GENERAL

The logic devices shown in FIGS. 4, 5 and 6 are all commercially available components. For example, the D-type flip-flops such as flip-flops 500, 502, 508, 510 and 512, 276, 288, 448, 414, etc., may be the type CD 4013M/CD 4013C dual D-type flip-flops manufactured and sold by the National Semiconductor Corporation. As such, they comprise monolithic complementary MOS integrated circuit constructed with N and P channel enhancement transistors. The logic level present at the "D" input is transferred to the Q output during the positive going transition of the clock pulse. Setting or resetting is independent of the clock and is accomplished by a high level on the set or reset line respectively. The rate and width counters 210, 216, 262 and 264 may comprise type CD4029M/CD4029C presettable, binary/decade, up/down counters also manufactured by the National Semiconductor Corporation. A logical "1" preset enable signal to such a counter allows information at the "jam" inputs to preset the counter to any state asynchronously with the clock. The counter is advanced one count at the positive-going edge of the clock if the carry-in and preset enable inputs are at logical "0" levels. Advancement is inhibited when either or both of these two inputs is at a logical "1" level. The "carry out" signal is normally at its logical "1" state and goes to the logical "0" state when the counter reaches its maximum count in the "up" mode or the minimum count in the "down" mode, provided the carry input is at logical "0" state. The program interval counter 462 may be implemented with the National Semiconductor Corporation type CD4040M/CD4040C counter. This is a 12 stage ripple-carry binary counter having buffered outputs from each stage externally available. The counter is reset to its logical "0" state by a logical "1" applied to its reset input terminal. The counter is advanced 1 count on the negative transition of each clock pulse.

NAND gates, NOR gates, AND gates and OR gates are also commercially available in integrated circuit technology.

From the above description, it is apparent that the apparatus of the present invention provides a pulse generator capable of providing artificial stimulating electrical pulses in the absence of normal heart activity, with the pulse rate and pulse width of such stimulating signals being programmable by an externally located mechanism. The digital implementation lends itself to microminiaturization which is, of course, a desired feature in implanted stimulator devices. The device of the present invention also incorporates requisite safety features to prevent inadvertent or spurious operation thereof to the detriment of the user.

While there have been disclosed and described what at present is considered to be the preferred embodiment of the present invention, it will be obvious to those skilled in the art that various changes and modifications may be made therein without departing from the invention and it is believed in the appended claims to cover all such changes and modifications as fall within the true specification and scope of the invention.

I claim:

1. In an implantable heart pacer of the type including a variable rate pulse generator for applying artificial heart stimulating pulses at a desired rate of the heart of a patient in the absence of normal heart activity, means for changing the repetition rate of the pulses produced by said pulse generator from a first value to a second desired value, comprising:
    (a) a register adapted to store a digital value corresponding to a desired pulse repetition rate;
    (b) a digital counting means having inputs and outputs;
    (c) magnetically actuable means responsive to the presence of an applied magnetic field for generating a code corresponding to a second desired pulse repetition rate;
    (d) multiplexer means connected between said register, said magnetically actuable means and said inputs of said digital counting means for selectively transferring the contents of said register of said digital code corresponding to a second desired pulse repetition rate to said digital counting means; and
    (e) means coupling said outputs of said digital counting means to said variable rate pulse generator.

2. Apparatus as in claim 1 and further including:
    (a) a source of electrical potential for providing energization of said implantable heart pacer;
    (b) circuit means coupled to said source of electrical potential for sensing the voltage output of said source; and
    (c) means including said magnetically actuable means coupling said circuit means to said multiplexer for entering a predetermined binary code pattern into said digital counting means indicative of the voltage output of said source, the arrangement being such that the rate at which said heart stimulating pulses are produced when said externally applied magnetic field is present is indicative of the voltage output of said source.

3. An implantable heart pacer for applying artificial heart stimulating pulses at a desired pre-programmed rate to the heart of a patient in the absence of normal heart activity comprising in combination:
    (a) variable rate pulse generator means having a resettable timing means determining a desired delay period between successive ones of said heart stimulating pulses; and
    (b) a refractory period establishing means comprising;
        (1) an N-stage binary counter having a reset terminal, a counter input terminal and a plurality of output terminals associated with predetermined stages of said N-stage counter;
        (2) a source of regularly occuring clock signals;
        (3) gating means connected to said counter input terminal and having an input line connected to receive said regularly occurring clock signals from said source;
        (4) bistable circuit means having a set and a reset state and an output line coupled to said reset terminal of said N-stage binary counter, to an input of said gating means and to said resettable timing means;
        (5) means coupling one of said plurality of output terminals of said N-stage binary counter to said bistable circuit means for switching said bistable circuit means to said reset state when the number of clock signals applied to said counter reachs a predetermined value;
        (6) means for switching said bistable circuit means to said set state in response to a naturally occurring heart stimulating pulse;
        (7) a further bistable circuit means having a set state, a reset state, an output terminal, a set input terminal and a reset input terminal;
        (8) a coincidence gate having its input terminal connected to predetermined ones of said plurality of output terminals of said N-stage counter and its output terminal coupled to the reset terminal of said further bistable circuit means;
        (9) means connecting said output terminal of said further bistable circuit means to said bistable circuit means for switching said bistable circuit means from its reset state to its set state and for enabling said gating means until said coincidence gate provides a reset signal to said further bistable circuit means; and
        (10) means responsive to the generation of said artificial heart stimulating pulses for switching said further bistable circuit means to its set state.

4. An implantable heart pacer for applying artifical heart stimulating pulses of a predetermined pulse width and repetition rate to the heart of a patient comprising:
- (b) a first binary register for storing a first predetermined binary number value corresponding to a desired stimulating pulse repetition rate, said first binary register having a plurality of outputs for carrying signals indicative of said first binary number value;
- (b) a second binary register for storing a second predetermined binary number value corresponding to a desired stimulating pulse width said second binary register having a plurality of outputs for carrying signals indicative of said second binary number value;
- (c) a first presettable counter having a clock input terminal, a load enable input terminal, a carry output terminal and a plurality of input terminals operatively coupled to said outputs of said first binary register for periodically receiving said first binary number value each time its load enable input terminal is stimulated;
- (d) a second presettable counter having a clock input terminal, a carry output terminal, a load enable input terminal and a plurality of input terminals operatively coupled to said outputs of said second binary register for periodically receiving said second binary number value each time its load enable input terminal is stimulated;
- (e) a source of regularly occurring timing signals coupled to said clock input terminals of said first and second presettable counters for changing the numbers stored therein at a fixed rate;
- (f) means coupling said carry output terminal of said first presettable counter to said load enable terminals of said first and second presettable counter; and
- (g) means coupling said carry output terminals of said first and second presettable counters to the heart of the patient; the arrangement being such that when said first binary number value initially in said first presettable counter is changed by said timing signals to a given value, a heart stimulating pulse is initiated and when said second binary number value entered into said second presettable counter is changed by said timing signals to a given value, said heart stimulating pulse is terminated.

5. The pacer as in claim 4 and further including:
- (a) digital logic means responsive to binary pulse code patterns generated external to the body of a patient for producing an enabling signal only when pulse code patterns of predetermined binary significance are received during a preset time interval; and
- (b) means coupling said digital logic means to said first and second binary registers and responsive to said enabling signal for enabling the storing of a new digital value in said first and second binary registers.

6. Apparatus as in claim 4 and further including:
- (a) a digital multiplexer means having first and second sets of input data terminals and a signal set of output terminals, said multiplexer means having said first set of input terminals connected to the output of said first binary number register and said single set of output terminals connected to the input terminals of said first presettable counter;
- (b) magnetically actuable means responsive to the presence of an externally applied magnetic field for generating digital codes of predetermined significance indicative of voltage magnitude; and
- (c) means coupling said magnetically actuable means to said second set of input data terminals of said digital multiplexer.

7. Apparatus as in claim 6 and further including:
- (a) means connected to the plural outputs of said first binary number register for sensing the magnitude of said new digital value entered therein; and
- (b) means responsive to said sensing means and coupled to said magnetically actuable means for causing a code of predetermined significance to be applied to said second set of input data terminals of said digital multiplexer when the magnitude of said new digital value lies outside of upper and lower limits.

8. Apparatus as in claim 4 and further including:
- (a) counter reset means responsive to the occurrence of a natural heartbeat for stimulating said load enable input terminal of said first pdresettable counter only if said natural heatbeat occurs subsequent to a predetermined period following the next preceding one of said natural heartbeats.

9. Apparatus as in claim 8 wherein said counter reset means comprises:
- (a) electrode means coupled to the heart of the patient;
- (b) amplifier means having input terminals coupled to said electrode means and an output terminal;
- (c) digital timing means including a third digital counter having a clock input terminal coupled through first gating means to said source of regularly occurring timing signals, a reset terminal and a plurality of output terminals;
- (d) a bistable flip-flop having an input terminal coupled to said output terminal of said amplifier and an output coupled through second gating means to said reset terminal of said third digital counter and to said first gating means; and
- (e) third gating means coupled to said plurality of output terminals of said third digital counter for inhibiting stimulation of said load enable input terminal of said first presettable counter until the number of timing signals accumulated in said third digital counter following the setting of said flip-flop reaches a predetermined value.

10. Apparatus as in claim 9 and further including:
- (a) noise sensing means coupled to the output of said amplifier means, and to said second and third gating means for resetting said third digital counter upon the detection of noise during the period that said third digital counter is accumulating timing pulses and prior to the time when said third digital counter reaches said predetermined value.

* * * * *

UNITED STATES PATENT AND TRADEMARK OFFICE
CERTIFICATE OF CORRECTION

PATENT NO. : 4,304,238                          Page 1 of 3

DATED : December 8, 1981

INVENTOR(S) : David J. Fischer

It is certified that error appears in the above-identified patent and that said Letters Patent are hereby corrected as shown below:

Column 1, Line 10, before the word "now" the word -- both -- should be added. Line 63, the word "ate" should read -- rate --.

Column 2, Line 13, the word "attenuated" should read -- attenuates --.

Column 4, Line 41, the word "serve" should read -- serves --.

Column 5, Line 32, the word "outut" should read -- output --. Line 34, the word "as" should read -- a --.

Column 7, Line 48, "ap" should be deleted.

Column 8, Line 51, the word "of" should read -- to --.

Column 11, Line 23, the word "outut" should read -- output --.

Column 12, Line 12, the word "speecifically" should read -- specifically --. Line 47, "Q" should read -- $\overline{Q}$ --. Line 52, "Q" should read -- $\overline{Q}$ --. Line 53, the word "fli-flop" should read -- flip-flop --. Line 54, "Q" should read -- $\overline{Q}$ --. Line 61, the word "The" should read -- The --. Line 63, the words "Width Count" should read -- Width Count --. Line 66, the words "width Reset" should read -- Width Reset --.

UNITED STATES PATENT AND TRADEMARK OFFICE
CERTIFICATE OF CORRECTION

PATENT NO. : 4,304,238

DATED : December 8, 1981

INVENTOR(S) : David J. Fischer

It is certified that error appears in the above-identified patent and that said Letters Patent are hereby corrected as shown below:

Column 13, Line 3, "Q" should read -- $\overline{Q}$ --. Line 22, the words "Mag Rate" should read -- $\overline{\text{"Mag Rate"}}$ --. Line 24, the numeral "30" should be deleted. Line 67, "Q" should read -- $\overline{Q}$ --.

Column 14, Line 15, before the word "gate" the words -- last-mentioned -- should be added. Line 33, the word "state" should read -- stage --.

Column 15, Line 22, in the sub-title under "Operation", the word "Faced" should read -- Paced --. Line 38, the word "or" should read -- of --.

Column 16, Line 1, the word "it" (second occurrence) should read -- It --. Line 23, the numeral "37" should be deleted. Line 43, "FPET's" should read -- FET's --.

Column 18, Line 12, the word "signal" should read -- signals --. Line 61, the word "assures" should read -- assure --.

Column 20, Line 53, "Q" should read -- $\overline{Q}$ --.

Column 22, Line 24, "Q" should read -- $\overline{Q}$ --. Line 42, "Q" should read -- $\overline{Q}$ --.

UNITED STATES PATENT AND TRADEMARK OFFICE
CERTIFICATE OF CORRECTION

PATENT NO. : 4,304,238

DATED : December 8, 1981

INVENTOR(S) : David J. Fischer

It is certified that error appears in the above-identified patent and that said Letters Patent are hereby corrected as shown below:

Column 23, Line 49, the word "of" (first occurrence) should read -- to --.

Column 25, Line 3, after the word "patient" a comma (,) should be inserted. Line 61, the word "a" should be deleted. Line 62, the word "signal" should read -- single --.

Column 26, Line 27, the word "pdressettable" should read -- presettable --.

Signed and Sealed this

Twenty-seventh Day of April 1982

[SEAL]

Attest:

Attesting Officer

GERALD J. MOSSINGHOFF

*Commissioner of Patents and Trademarks*